(12) United States Patent
Bywater-Ekegard

(10) Patent No.: US 10,561,149 B2
(45) Date of Patent: Feb. 18, 2020

(54) MICROBIAL COMPOSITIONS AND METHODS FOR BIOPROTECTION

(71) Applicant: CONCENTRIC AG CORPORATION, Centennial, CO (US)

(72) Inventor: Margaret Bywater-Ekegard, Lac Brome (CA)

(73) Assignee: CONCENTRIC AG CORPORATION, Centennial, CO (US)

( * ) Notice: Subject to any disclaimer, the term of this patent is extended or adjusted under 35 U.S.C. 154(b) by 0 days.

(21) Appl. No.: 15/571,157

(22) PCT Filed: May 2, 2016

(86) PCT No.: PCT/IB2016/000675
§ 371 (c)(1),
(2) Date: Nov. 1, 2017

(87) PCT Pub. No.: WO2016/178086
PCT Pub. Date: Nov. 10, 2016

(65) Prior Publication Data
US 2018/0255786 A1 Sep. 13, 2018

Related U.S. Application Data

(60) Provisional application No. 62/155,955, filed on May 1, 2015.

(51) Int. Cl.
*A01N 63/02* (2006.01)
*C05F 5/00* (2006.01)
*C05G 3/06* (2006.01)
*C12R 1/01* (2006.01)

(52) U.S. Cl.
CPC .............. *A01N 63/02* (2013.01); *C05F 5/008* (2013.01); *C05G 3/06* (2013.01); *C12R 1/01* (2013.01)

(58) Field of Classification Search
None
See application file for complete search history.

(56) References Cited

U.S. PATENT DOCUMENTS

| | | | |
|---|---|---|---|
| 5,578,486 A | 11/1996 | Zhang | |
| 5,667,779 A | 9/1997 | Kubo | |
| 6,025,187 A | 2/2000 | Penaud | |
| 6,326,016 B2 * | 12/2001 | Moesinger | A01N 63/04 424/405 |
| 6,905,288 B2 | 6/2005 | Miyazaki | |
| 7,811,353 B2 | 10/2010 | Blais | |
| 9,175,258 B2 | 11/2015 | Bywater-Ekegard et al. | |
| 2001/0014324 A1 | 8/2001 | Moesinger | |
| 2009/0011491 A1 * | 1/2009 | Barnabe | A01N 63/04 435/252.5 |
| 2012/0015806 A1 | 1/2012 | Paikray et al. | |
| 2012/0031157 A1 | 2/2012 | Paikray | |
| 2013/0205849 A1 | 8/2013 | Kloepper et al. | |
| 2016/0100587 A1 | 4/2016 | Bywater-Ekegard et al. | |
| 2016/0102251 A1 | 4/2016 | Bywater-Ekegard et al. | |

FOREIGN PATENT DOCUMENTS

| | | |
|---|---|---|
| CN | 1721345 A | 1/2006 |
| CN | 101186879 A | 5/2008 |
| CN | 101591679 A | 12/2009 |
| CN | 101698539 A | 4/2010 |
| JP | S5319673 A | 2/1978 |
| KR | 20040006045 A | 1/2004 |
| RU | 2322061 C2 | 4/2008 |
| WO | WO 2007/150052 A1 | 12/2007 |
| WO | WO 2011/157747 A2 | 12/2011 |
| WO | WO-2012/101528 A2 | 8/2012 |

OTHER PUBLICATIONS

Abbasi, P., et al., "Detection of High Concentrations of Organic Acids in Fish Emulsion and Their Role in Pathogen or Disease Suppression," Phytopathology, 2009, pp. 274-281, vol. 99, No. 3.
Adam et al., "Bacterial Antagonists of Fungal Pathogens Also Control Root-Knot Nematodes by Induced Systemic Resistance of Tomato Plants", (2014) PLoS ONE 9(2): e90402. Published Feb. 28, 2014.
Bankar AV, et al. (2009) Environmental and industrial applications of Yarrowia lipolytica. Applied Microbiology and Biotechnology, 84(5): 847:865.
Bankar AV, et al. (2009) Removal of chromium {VI} ions from aqueous solution by absorption into two marine isolates of Yarrowia lipolytica. Journal of Harzardous Materials, 170(1 ): 487-494.
Bay, J.C., "The Spore-Forming Species of the Genus *Saccharomyces*", The American Naturalist, Aug. 1893, pp. 685-696, vol. 27.
Communication pursuant to Article 94(3) EPC for European Patent Application No. EP 12739612.5, dated Jan. 12, 2017, 5 Pages.
Communication pursuant to Article 94(3) EPC for European Patent Application No. EP 12739612.5, dated Nov. 30, 2017, 5 Pages.
Conn, K., et al., "Liquid Swine Manure Can Kill Verticillum dahliae Microsclerotia in Soil by Volatile Fatty Acid, Nitrous Acid, and Ammonia Toxicity," Phytopathology, 2005, pp. 28-35, vol. 95, No. 1.
Cook, K.L., "Optimizing Culturing Conditions for *Bacillus subtilis*," South African Avocado Growers' Association Yearbook 1996, vol. 19, pp. 54-58.
El-Kholy et al., "Autolysis and intracellular enzyme release from cheese related dairy lactobacilli", Lait 1998, vol. 78, pp. 439-452.
Examination Report No. 1 for Australian Patent Application No. AU-2016204301, dated Sep. 20, 2016, 3 Pages.
Examination Report No. 2 for Australian Patent Application No. AU-2016204301, dated May 10, 2017, 3 Pages.

(Continued)

*Primary Examiner* — Johann R Richter
*Assistant Examiner* — Danielle Sullivan
(74) *Attorney, Agent, or Firm* — Goodwin Procter LLP

(57) ABSTRACT

The present disclosure comprises compositions and methods for bioprotection, such as enhancing antimicrobial activity and decreasing abiotic stress. For example, the present disclosure comprises compositions and methods for affecting, enhancing, modulating, or decreasing antimicrobial activity.

21 Claims, 10 Drawing Sheets

(56) References Cited

OTHER PUBLICATIONS

Examiner's Report No. 1 for Canadian Patent Application No. CA-2,839,383, dated Jul. 25, 2017, 5 Pages.
Extended European Search Report for European Patent Application No. EP 12739612.5, dated Jan. 20, 2016, 11 Pages.
Fickers P, et al. (2005) Hydrophobic substrate utilisation by the yeast Yarrowia lipolytica, and its potential applications. FEMS Yeast Research, 5(6-7): 527-543.
First Examination Report issued by the Australian Patent Office dated Mar. 18, 2015 for Australian Application No. 2012210260 filed on Jan. 12, 2012.
First Office Action issued by the State Intellectual Property Office of the People's Republic of China dated Sep. 3, 2014 for Chinese Application No. 201280009159.9 filed on Jan. 12, 2012, which was published as 103649303A on Mar. 9, 2014.
Garbaye et al., New Phytol. (1994), 128, 197-210.
Garcia-Kirchner, O., et al., "Mixed Submerged Fermentation with Two Filamentous Fungi for Cellulolytic Andxylanolytic Enzyme Production", Applied Biochemistry and Biotechnology, vol. 98-100, 2002, pp. 1105-1114.
Harwood CS, et al. (1986) Uptake of Benzoate by Rhodopseudomonas palustris Grown Anaerobically in Light. J. Bacteriology, 165(2): 504-509.
Harwood CS, et al. (1999) Anaerobic metabolism of aromatic compounds via the benzoyl-CoA pathway. FEMS microbiology Reviews, 22: 439-458.
International Preliminary Report on Patentability issued by the International Searching Authority dated Jul. 27, 2013 for PCT/IB2012/000833 filed Jan. 12, 2012 and published as WO 2012/101528 on Aug. 2, 2012, 9 pages.
International Search Report issued by the International Searching Authority dated Aug. 10, 2012 for PCT/IB2012/000833 filed Jan. 12, 2012 and published as WO 2012/101528 on Aug. 2, 2012, 3 pages.
Jain MR, et al. (2004) 2,4,6-trinitrotoluene transformation by a tropical marine yeast, Yarrowia liplytica NCIM 3589. Marine Pollution Bulletin, 49(9-10): 783-788.
Kumar, S.K., et al., "Continuous hydrolysis of raffinose family oligosaccharides in soymilk by fluidized bed reactor", LWT—Food Science and Technology, Aug. 19, 2009, pp. 220-225, vol. 43, No. 2.
Lee et al., "Unique Properties of Four Lactobacilli in Amino Acid Production and Symbiotic Mixed Culture for Lactic Acid Biosynthesis", Current Microbiology 2001, vol. 43, pp. 383-390.
McKellar, M., et al., "Compost-Induced Suppression of Pythium Damping-Off is Mediated by Fatty-Acid-Metabolizing Seed-Colonizing Microbial Communities," Applied and Environmental Microbiology, Jan. 2003, pp. 452-460, vol. 69, No. 1.
Mukherjee, AK. et al., "Bioremediation and reclamation of soil contaminated with petroleum oil hydrocarbons by exogenously seeded bacterial consortium: a pilot-scale study", Environmental Science and Pollution Research, Sep. 2010, vol. 18, pp. 471-478.
Nam, et al. (2003) A novel catabolic activity of Pseudomonas veronii in biotransformation of pentachlorophenol. Applied microbiology and Biotechnology, 62(2-3): 284-290.
Non-Final Office Action dated Mar. 12, 2015 for U.S. Appl. No. 13/979,419, filed Jan. 6, 2014, 18 pages.
Non-Final Office Action dated Nov. 14, 2014 for U.S. Appl. No. 13/979,419, filed Jan. 6, 2014, 11 pages.
Onaca, et al. (2007) Degradation of alkyl; methyl ketones by Pseudomonas vernil. Journal of Bacteriology, 189(10): 3759-3767.
Piggot, P., "Spore development in Bacillus subtilis", Current Opinion in Genetics & Development, Nov. 1996, pp. 531-537, vol. 6, No. 5.
Rokas A. (2009) The effect of domestication on the fungal proteome. Trends in Genetics: TIG, 25(2): 60-63.
Schennen U, et al. (1985) Anaerobic degradation of 2 fluorobenzoate by benzoate-degrading, denitrifying bateria. J_ Bacteriol., 161 (1 ): 321-325.
Second Office Action issued by the State Intellectual Property Office of the People's Republic of China dated Jul. 14, 2015 for Chinese Application No. 201280009159.9, 7 pages.
Shim, Y. H., et al., "Evaluation of Multi-Microbial Probiotics Produced by Submerged Liquid and Solid Substrate Fermentation Methods in Broilers", Asian Australas. J. Anim. Sci., vol. 23, No. 4, Apr. 2010, pp. 521-529.
Taher DM, et al. (2009) Comparison of normal composting with composting using effective microorganisms for poultry carcasses disposal in poultry farms. Iraqi Journal of Veterinary Sciences, 23(2): 1607-3994.
Tenuta, M., et al., "Volatile Fatty Acids in Liquid Swine Manure Can Kill Microsclerotia of Verticillium Dahliae," Phytopathology, 2002, pp. 548-552, vol. 92, No. 5.
Third Office Action for Chinese Application No. CN 201280009159. 9, dated Apr. 6, 2016, 8 Pages.
Wang, C., et al., "Microorganisms in Daqu: a Starter Culture of Chinese Maotai-flavor liquor", World Journal of Microbiology and Biotechnology, Kluwer Academic Publishers, So, vol. 24, No. 10, Mar. 24, 2008, pp. 2183-2190.
Widmer, T.L., et al., "Composted Municipal Waste Reduces Infection of Citrus Seedlings by Phytophthora nicotianae," Plant Disease, Jun. 1998, pp. 683-688, vol. 82, No. 6.
Written Opinion issued by the International Searching Authority dated Aug. 10, 2012 for PCT/IB2012/000833 filed Jan. 12, 2012 and published as WO 2012/101528 on Aug. 2, 2012, 8 pages.
Ying, Liu, et al., Review on Degradation and Conversion of Environmental Pollutants by Mycorrhizal Fungi. Shanghai Environmental Sciences, vol. 17, No. 2, pp. 127-131.
PCT International Search Report & Written Opinion, International Application No. PCT/IB2016/000675, dated Sep. 8, 2016, 11 Pages.

\* cited by examiner

MICROBIAL COMPOSITIONS AND METHODS FOR BIOPROTECTION

CROSS-REFERENCE TO RELATED APPLICATIONS

This application is the National Stage of International Application No. PCT/IB32016/000675, filed May 2, 2016, which claims the benefit of U.S. Provisional Application No. 62/155,955, filed May 1, 2015, each of which is herein incorporated in its entirety by reference.

TECHNICAL FIELD

The disclosure herein relates to plant bioprotectant compositions and methods of producing and using the same. In various aspects, the present disclosure relates to methods for effectively improving antimicrobial activity, including, for example, but not limited to, antifungal, antiviral, and antibacterial activity, by application of disclosed plant bioprotectant compositions.

BACKGROUND OF THE INVENTION

While agrochemicals have raised agricultural productivity levels, the excessive and inappropriate use of agrochemicals, such pesticides, can result in negative and sometimes irreparable effects on soil health and the environment. As such, farmers and consumers are now in search of safe, secure, and sustainable alternatives to agrochemicals that would provide safe and high productivity levels without harm to the environment. Among such approaches that are a focus of ongoing research in the agricultural sector is the use of biological control agents, also referred to as bioprotectants. A key focus of research in the area of bioprotectants is the identification, development, and manipulation of unique combinations of biological organism and/or their metabolites in order to achieve desired product profiles, e.g., unique antipathogen profiles.

Exemplary plant bioprotectants include, but are not limited to, compositions based on bacteria (i.e., Mycostop, Galltroll-A, Companion, Serenade, Kodiak, and Deny), fungi (i.e., RootShield, SoilGard, Trichodex, and AQ10), and insects. These bioprotectants may act via a single- or multi-mode of action including competition, antagonism, antibiosis, stimulation of plant systemic resistance reactions, and attack and consumption of fungal resting structures. Plant bioprotectants are used to treat crops in a commercial setting, in part, due to their ability improve antifungal, antiviral, and/or antibacterial activity.

Despite advances in the development of bioprotectants, there remains a need for compositions and methods that can perform plant bioprotection, e.g., protection of plants from plant microbial pathogens, while reducing the use of agrochemicals. These needs and other needs are addressed by the present disclosure.

SUMMARY

Disclosed herein are compositions and methods for plant bioprotection, e.g., protecting biological plants from pathological damage from microorganisms such as bacteria, viruses and fungi, and from reduced growth and vigor due to abiotic stress. In various aspects, the disclosure pertains to methods comprising using a bioprotectant composition comprising a cell-free supernatant derived from a microbial fermentation culture inoculated with a mixture of microorganisms.

Disclosed are methods for bioprotection comprising providing a bioprotectant composition comprising cell-free supernatant derived from a microbial fermentation culture inoculated with one or more isolated microorganism, wherein the microorganism comprises *Aspergillus* spp., for example, *Apergillus oryzae*, IN-AO1, deposited Sep. 4, 2014 with ATCC, PTA-121551; *Bacillus* spp., for example, *Bacillus subtilis*, IN-BSI, deposited Jan. 11, 2012 with ATCC, PTA-12385; *Rhodopseudomonas* spp., for example, *Rhodopseudomonas palustris*, IN-RPI, deposited Jan. 11, 2012 with ATCC, PTA-12387; *Rhodopseudomonas palustris*, IN-RP2, deposited Sep. 4, 2014 with ATCC, PTA-121533; *Candida* spp., for example, *Candida utilis*, IN-CU1, deposited Sep. 4, 2014 with ATCC, PTA-12550; *Lactobacillus* spp., for example, *Lactobacillus helveticus*, IN-LHI, deposited Jan. 11, 2012, with ATCC, PTA 12386; *Lactobacillus rhamnosus*, IN-LR1, deposited Sep. 4, 2014 with ATCC, PTA 121554; *Lactobacillus casei*, IN-LC1, deposited Sep. 4, 2014 with ATCC, PTA-121549; *Lactobacillus plantarum*, IN-LP1, deposited Sep. 4, 2014 with ATCC, PTA 121555; *Lactococcus* spp., for example, *Lactococcus lactis*, IN-LL1, deposited Sep. 4, 2014 with ATCC, PTA-121552; *Pseudomonas* spp., for example, *Pseudomonas aeuroginosa* or *Pseudomonas fluorescens*; *Saccharomyces* spp., for example, *Saccharomyces cerevisiae*, IN-SCI, deposited on Jan. 11, 2012 with ATCC, PTA-12384; or *Streptococcus* spp., for example, *Streptococcus lactis*; or combinations thereof, or a microbial consortia comprising one or more of the above, for example, IN-M1, deposited Jan. 11, 2012 with ATCC, PTA-12383 and/or IN-M2, deposited Sep. 4, 2014 with ATCC, PTA-121556, to a plant seed, to a plant fruit, to a plant, or to a plant at a particular growth stage, or combinations thereof, or to the soil or a plant growth media in which a plant, seed or plant part can be planted or grown, thereby providing bioprotection to the plant, seed, fruit or other plant parts.

BRIEF DESCRIPTION OF THE FIGURES

The accompanying figures, which are incorporated in and constitute a part of this specification, illustrate several aspects and together with the description serve to explain the principles of the invention.

Figure 1A:
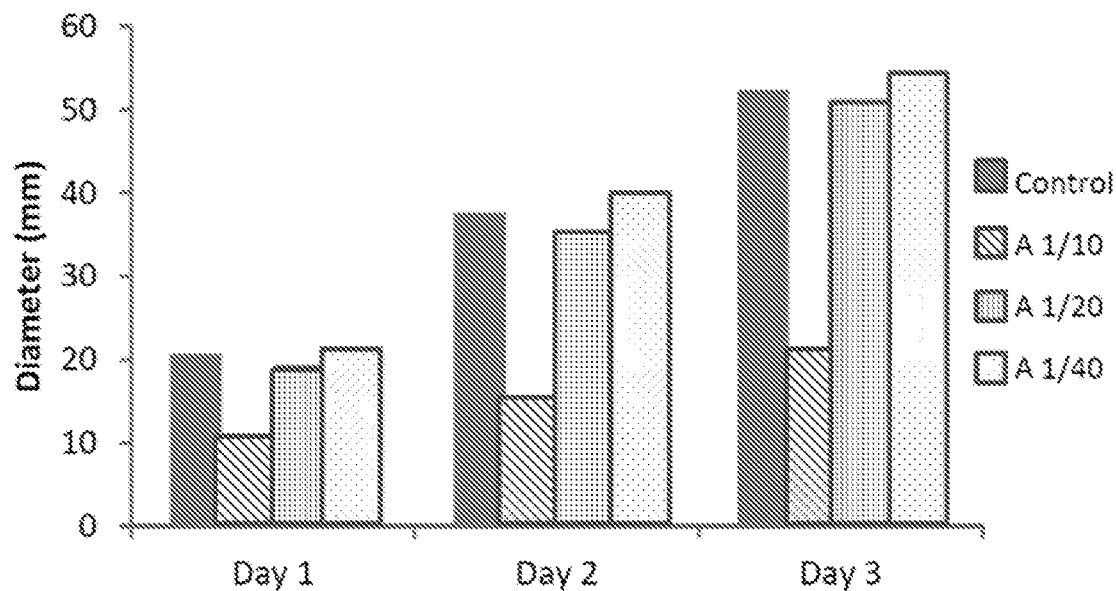
FIGS. 1A and 1B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (1B) on the growth of *P. capsici* at pH 7.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The disclosure can be understood more readily by reference to the following detailed description and the Examples included therein. Although any methods and materials similar or equivalent to those described herein can be used in the practice or testing of the present disclosure, example methods and materials are now described.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The terminology used herein is for the purpose of describing particular aspects only and is not intended to be limiting. In this specification and in the claims which follow, reference will be made to a number of terms which shall be defined to have the following meanings:

As used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

The word "or" as used herein means any one member of a particular list and also includes any combination of members of that list.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

As used herein, the terms "effective amount", "effective concentration", or "effective dosage" is intended to mean the amount, concentration, or dosage of a bioprotectant composition to cause improved antimicrobial activity. The actual effective dosage in absolute value depends on factors including, but not limited to, the size (e.g., the area, the total acreage, etc.) of the land for application with the bioprotectant composition. The "effective amount", "effective concentration", or "effective dosage" of a biostimulant composition may be determined, e.g., by a routine dose response experiment.

As used herein, the term "carrier" is intended to refer to an "agronomically acceptable carrier." An "agronomically acceptable carrier" is intended to refer to any material which can be used to deliver a bioprotectant composition as described herein, agriculturally beneficial ingredient(s), biologically active ingredient(s), etc., to a plant, a plant part (e.g., a seed), or a soil, and preferably which carrier can be added (to the plant, plant part (e.g., seed), or soil) without having an adverse effect on plant growth, soil structure, soil drainage or the like.

As used herein, the term "soil-compatible carrier" is intended to refer to any material which can be added to a soil without causing/having an adverse effect on plant growth, soil structure, soil drainage, or the like.

As used herein, the term "foliar-compatible carrier" is intended to refer to any material which can be added to a plant or plant part without causing/having an adverse effect on the plant, plant part, plant growth, plant health, or the like.

As used herein, the term "micronutrient(s)" is intended to refer to nutrients which are needed for plant growth, plant health, and/or plant development.

As used herein, the term "herbicide(s)" is intended to refer to any agent or combination of agents capable of killing weeds and/or inhibiting the growth of weeds (the inhibition being reversible under certain conditions).

As used herein, the term "fungicide(s)" is intended to refer to any agent or combination of agents capable of killing fungi and/or inhibiting fungal growth.

As used herein, the term "insecticide(s)" is intended to refer to any agent or combination of agents capable of killing one or more insects and/or inhibiting the growth of one or more insects.

As used herein, the term "agriculturally beneficial ingredient(s)" is intended to mean any agent or combination of agents capable of causing or providing a beneficial and/or useful effect in agriculture.

As used herein, "at least one biologically active ingredient" is intended to mean biologically active ingredients (e.g., signal molecules, other microorganisms, etc.) other than the one or more bacterial isolates described herein.

As used herein, the term "determining" can refer to measuring or ascertaining a quantity or an amount or a change in activity. For example, determining the characteristics of microorganisms or growing cultures as used herein can refer to the steps that the skilled person would take to measure or ascertain some quantifiable value in a sample. The art is familiar with the ways to measure characteristics in a sample. The term sample is used in its common meaning of a portion from a larger solution, from a site, from a culture, or other larger entity from which a portion, the sample, can be removed and optionally acted upon.

The term "bioprotection," as used herein, refers to the enhancement of resistance of a plant to pathological actions by one or more microbial organisms, and is such protection is compared to a similar, control plant not treated with a bioprotectant composition disclosed herein. Bioprotection can include reduction of plant pathogen damage due to plant pathogens and reduction of abiotic stress. Such bioprotection may include an antimicrobial response by a plant, in which the enhanced antimicrobial response may be due to enhanced activities or response by the plant to resist one or more microorganisms or the bioprotection may be due to actions by components of compositions applied to the plant against one or more microorganisms. In a particular context, bioprotection refers to processes that improve the antimicrobial activity or response of plants, e.g., plants to which a bioprotectant is applied. Bioprotectant compositions may be delivered via a soil amendment(s). In an aspect, a bioprotectant composition of the present disclosure is a cell-free composition resulting from the supernatant of a microbial culture. In an aspect, a bioprotectant composition of the present disclosure is a cell-free composition resulting from the supernatant of a microbial culture, and such a cell-free compositions may further comprise one or more added microorganisms, which microorganisms can be the same as or different from the microorganisms of the microbial culture from which the cell-free compositions was made. Such compositions, when provided to plants, by any method including as a soil amendment, may provide microoganisms as part of a consortium to reside on or in the plant as an endophyte or epiphyte.

As used herein, the term "bioprotectant(s)" is intended to refer to any composition capable of enhancing the antimicrobial activity of a plant, antinematocidal activity of a plant, a reduction in pathological symptoms or lesions resulting from actions of a plant pathogen, or a reduction in abiotic stress of a plant, compared to an untreated control plant. Unless clearly stated otherwise, a bioprotectant may be comprised of a single ingredient or a combination of several different ingredients, and the enhanced antimicrobial activity may be attributed to one or more of the ingredients, either acting independently or in combination.

The term, "environment" as used herein, is an area as defined by the situation and includes the biotic and abiotic elements, and the patterns of the interrelationships between the biotic elements, and between the biotic and abiotic elements which are found in the defined area. All three physical states, solids, liquids and gases, are included in the elements which make up the environment.

As used herein, the term "microorganism" includes, but is not limited to, bacteria, viruses, fungi, algae, yeasts, protozoa, worms, spirochetes, single-celled, and multi-celled organisms that are included in classification schema as prokaryotes, eukaryotes, Archea, and Bacteria, and those that are known to those skilled in the art.

As used herein, the term "enhanced antimicrobial activity" is intended to refer to improved efficacy or activity against microorganisms (e.g., viruses, bacteria, or fungi) that reduces or eliminates the (relative) number of active microorganisms or reduces the pathological results of a microbial infection. Thus, the term includes the terms "antiviral,"

"antibacterial," and "antifungal." An "antimicrobial agent," as used herein, refers to a bioprotectant agent that prevents or reduces infections or damages of a plant caused by a pathogenic microorganism.

As used herein, the term "antibacterial" is intended to refer to an efficacy or activity (i.e., of an agent or extract) that reduces or eliminates the (relative) number of active bacteria or reduces the pathological results of a bacterial infection. An "antibacterial agent," as used herein, refers to a bioprotectant agent that prevents or reduces in vitro and/or in vivo infections or damages of a plant caused by a pathogenic bacterium.

As used herein, the term "antiviral" is intended to refer to an efficacy or activity (i.e., of an agent or extract) that reduces or eliminates the (relative) number of active viruses or reduces the pathological results of a viral infection. An "antiviral agent," as used herein, refers to a bioprotectant agent that prevents or reduces in vitro and/or in vivo infections or damages of a plant caused by a pathogenic virus.

As used herein, the term "antifungal" is intended to refer to an efficacy or activity (i.e., of an agent or extract) that reduces or eliminates the (relative) number of active fungi or reduces the pathological results of a fungal infection. An "antifungal agent," as used herein, refers to a bioprotectant agent that prevents or reduces in vitro and/or in vivo infections or damages of a plant caused by a pathogenic fungus.

As used herein, the terms "plant(s)" and "plant part(s)" are intended to refer to all plants and plant populations such as desired and undesired wild plants or crop plants (including naturally occurring crop plants), horticultural plants, hydroponic plants, aquatic plants, and any organism classified in the Plant kingdom. Crop plants can be plants, which can be obtained by conventional plant breeding and optimization methods or by biotechnological and genetic engineering methods or by combinations of these methods, including the transgenic plants and including the plant cultivars protectable or not protectable by plant breeders' rights. Examples include monocots and dicots, As used herein, the term "plant" includes whole plants, explants, plant organs (i.e., leaves, stems, roots, etc.), seeds, and plant cells and progeny of the same. "Plant cell" includes without limitation seeds, suspension cultures, embryos, meristematic regions, callus tissue, leaves, shoots, gametophytes, sporophytes, pollen, and microspores.

Plants, Plant Cells, Plant Parts, Explants, Seeds, and Grain

Plant parts are to be understood as meaning all parts and organs of plants above and below the ground, such as shoot, leaf, flower and root, meristimatic areas of a plant, examples include leaves, needles, stalks, stems, flowers, fruit bodies, fruits, seeds, roots, tubers and rhizomes. The plant parts also include harvested material and vegetative and generative propagation material (e.g., cuttings, grafts, tubers, rhizomes, off-shoots and seeds, etc.).

As used herein, the terms "microorganism" or "microbial" cover any generally unicellular organism, which can be propagated and manipulated in a laboratory. In the present disclosure, the terms comprise bacteria and/or yeast and/or fungi. In the present disclosure, the term microorganism typically denotes a live microorganism, i.e., capable of propagation and/or having metabolic activity.

As used herein, the term "strain" refers in general to a closed population of organisms of the same species. Accordingly, the term "strain of lactic acid bacteria" generally refers to a strain of a species of lactic acid bacteria. More particularly, the term "strain" refers to members of a microbial species, wherein such members, i.e., strains, have different genotypes and/or phenotypes. Herein, the term "genotype" encompasses both the genomic and the recombinant DNA content of a microorganism and the microorganism's proteomic and/or metabolomic profile and post translational modifications thereof. Herein, the term "phenotype" refers to observable physical characteristics dependent upon the genetic constitution of a microorganism. As one skilled in the art would recognize, microbial strains are thus composed of individual microbial cells having a common genotype and/or phenotype. Further, individual microbial cells may have specific characteristics (e.g., a specific rep-PCR pattern) which may identify them as belonging to their particular strain. A microbial strain can comprise one or more isolates of a microorganism.

As used herein, the term "inoculum" is intended to mean any form of microbial cells, or spores, which is capable of propagating in a culture medium.

The term "microbial composition" intends to refer to a composition of microorganisms as defined herein, which are used to inoculate the cultures and used in the methods as described herein.

As used herein, the term "isolate" refers to cultured microorganisms grown from a single colony taken from a primary isolation plate. An isolate is presumed to be derived from a single microorganism.

As used herein, the term "isolated" as applied to a microorganism refers to a microorganism which has been removed and/or purified from an environment in which it naturally occurs. As such, an "isolated strain" of a microbe as used herein is a strain that has been removed and/or purified from its natural milieu. Thus, an "isolated microorganism" does not include one residing in an environment in which it naturally occurs. Further, the term "isolated" does not necessarily reflect the extent to which the microbe has been purified. Note that a strain associated with other strains, or with compounds or materials that it is not normally found with in nature, is still defined as "isolated."

As used herein, the term "substantially pure culture" refers to a strain or culture which contains substantially no other microbes than the desired strain or strains of microbe. In other words, a substantially pure culture of a strain of microbe is substantially free of other contaminants, which can include microbial contaminants as well as undesirable chemical contaminants.

As used herein, the term "biologically pure culture" is intended to mean a culture essentially free from biological contamination and having a genetic uniformity such that different subcultures taken therefrom will display substantially identical genotypes and phenotypes (e.g., cultures have a purity of at least 60%, of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, up to 100% pure). Further, as used herein, a "biologically pure" strain is intended to mean a strain separated from materials with which it is normally associated in nature.

Culture medium as used herein is defined as a mixture which supports the growth of microbial cells, such as disclosed microbes used to inoculate the culture used to prepare disclosed cell-free supernatant, said mixture contains ingredients such as peptone, soy peptone, molasses, potato starch, yeast extract powder, or combinations thereof.

It is also to be understood that the terminology used herein is for the purpose of describing particular aspects only and is not intended to be limiting. As used in the specification and in the claims, the term "comprising" can include the aspects "consisting of" and "consisting essentially of."

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. The publications discussed herein are provided solely for their disclosure prior to the filing date of the present application. Nothing herein is to be construed as an admission that the present disclosure is not entitled to antedate such publication by virtue of prior invention. Further, the dates of publication provided herein can be different from the actual publication dates, which can require independent confirmation.

Bioprotectant Compositions

In an aspect, bioprotectant compositions of the present disclosure comprise a cell-free supernatant of a microbial culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof, to a plant seed, to a plant fruit, to a plant, or to a plant at a particular growth stage, or combinations thereof, thereby providing bioprotection to the plant. In an aspect, the invention relates to a cell-free supernatant prepared by a disclosed method. In an aspect, a bioprotectant composition comprises a cell-free supernatant of a microbial culture inoculated with one or more isolated microorganism, wherein the microorganism comprises *Aspergillus* spp., for example, *Apergillus oryzae*, IN-AO1, deposited Sep. 4, 2014 with ATCC, PTA-121551; *Bacillus* spp., for example, *Bacillus subtilis*, IN-BSI, deposited Jan. 11, 2012 with ATCC, PTA-12385; *Rhodopseudomonas* spp., for example, *Rhodopseudomonas palustris*, IN-RPI, deposited Jan. 11, 2012 with ATCC, PTA-12387; *Rhodopseudomonas palustris*, IN-RP2, deposited Sep. 4, 2014 with ATCC, PTA-121533; *Candida* spp., for example, *Candida utilis*, IN-CU1, deposited Sep. 4, 2014 with ATCC, PTA-12550; *Lactobacillus* spp., for example, *Lactobacillus helveticus*, IN-LHI, deposited Jan. 11, 2012, with ATCC, PTA 12386; *Lactobacillus rhamnosus*, IN-LR1, deposited Sep. 4, 2014 with ATCC, PTA 121554; *Lactobacillus casei*, IN-LC1, deposited Sep. 4, 2014 with ATCC, PTA-121549; *Lactobacillus plantarum*, IN-LP1, deposited Sep. 4, 2014 with ATCC, PTA 121555; *Lactococcus* spp., for example, *Lactococcus lactis*, IN-LL1, deposited Sep. 4, 2014 with ATCC, PTA-121552; *Pseudomonas* spp., for example, *Pseudomonas aeuroginosa* or *Pseudomonas fluorescens*; *Saccharomyces* spp., for example, *Saccharomyces cerevisiae*, IN-SCI, deposited on Jan. 11, 2012 with ATCC, PTA-12384; or *Streptococcus* spp., for example, *Streptococcus lactis*; or combinations thereof, or a microbial consortia comprising one or more of the above, for example, IN-M1, deposited Jan. 11, 2012 with ATCC, PTA-12383 and/or IN-M2, deposited Sep. 4, 2014 with ATCC, PTA-121556, and providing a disclosed composition to a plant seed, to a plant fruit, to a plant, or to a plant at a particular growth stage, or combinations thereof, or to the soil or a plant growth media in which a plant, seed or plant part can be planted or grown, thereby providing bioprotection to the plant, seed, fruit or other plant parts.

In an aspect, the cell-free supernatant is filter-sterilized or sterilized by methods known to those of skill in the art.

In an aspect, a bioprotectant composition of the present disclosure may further comprise one or more additional or optional components, including but not limited to, herbicides, pesticides, fungicides, nutrient compounds, micorrhyzal fungus, microorganisms, peptides, proteins, carriers, or delivery components, or combinations thereof.

In an aspect, a bioprotectant composition may further comprise an herbicide. Exemplary herbicides include, but are not limited to, imidazolinone, sulfonylurea, glyphosate, glufosinate, L-phosphinothricin, triazine, benzonitrile, Dicamba (3,6-dichloro-o-anisic acid or 3,6-dichloro-2-methoxybenzoic acid), the active ingredient in herbicides such as BANVEL™ (BASF), CLARITY™ (BASF), and VANQUISH™ (Syngenta), pyrethrins and synthetic pyrethroids; azoles, oxadizine derivatives; chloronicotinyls; nitroguanidine derivatives; triazoles; organophosphates; pyrrols; pyrazoles; phenyl pyrazoles; diacylhydrazines; and carbamates. Additional examples of herbicides within some of the above-listed categories can be found in The Pesticide Manual, 12th Ed., C. D. S. Tomlin, Ed., British Crop Protection Council, Farnham, Surry, UK (2000).

In an aspect, a bioprotectant composition may further comprise a pesticide. Exemplary pesticides include, but are not limited to, any bacterial species (i.e., *Bacillus thuringiensis*), viruses (i.e., densoviruses), biocontrol pesticides, abamectin, phostoxin/fumitoxin, bifenthrin, carbaryl, chlorfenapyr, beta-cyfluthrin, cypermethrin, deltamethrin, dichlorvos, D-phenothrin, D-trans allethrin, resmethrin, methomyl, hydramethylnon, fenoxycarb, fipronil, imidacloprid, imidacloprid, lambda-cyhalothrin, malathion, methoprene, naled, nithiazine, P-dichlorobenzene, permethrin, permethrin-piperonyl butoxide, propetamphos, propoxur, pyrethrins, phenothrin, allethrin, hydroprene, resmethrin, spinosad, sumthrin, sumthrin-piperonyl butoxide, temephos, mosquito larvicide, pupicide, or any combination thereof.

In an aspect, a bioprotectant composition may further comprise a fungicide. Exemplary fungicides include, but are not limited to, Mefenoxam & Fludioxonil (ApronMaxx RTA, Syngenta USA), tebuconazole, simeconazole, fluquinconazole, difenoconazole, 4,5-dimethyl-N-(2-propenyl)-2-(trimethylsilyl)-3-thiophenecarboxamide (silthiopham), hexaconazole, etaconazole, propiconazole, triticonazole, flutriafol, epoxiconazole, fenbuconazole, bromuconazole, penconazole, imazalil, tetraconazole, flusilazole, metconazole, diniconazole, myclobutanil, triadimenol, bitertanol, pyremethanil, cyprodinil, tridemorph, fenpropimorph, kresoxim-methyl, azoxystrobin, ZEN90160, fenpiclonil, benalaxyl, furalaxyl, metalaxyl, R-metalaxyl, orfurace, oxadixyl, carboxin, prochloraz, trifulmizole, pyrifenox, acibenzolar-5-methyl, chlorothalonil, cymoaxnil, dimethomorph, famoxadone, quinoxyfen, fenpropidine, spiroxamine, triazoxide, BAS50001 F, hymexazole, pencycuron, fenamidone, guazatine, and cyproconazole.

In an aspect, a bioprotectant composition may further comprise a nutrient component. As used herein, the term "nutrient component" refers to a solid, including powders, granules, or pellets, or a liquid, including solutions or suspensions, which contains nutrients in the solution or in the mixture. The nutrient component is intended to comprise a material which enables plant growth.

In an aspect, a bioprotectant composition may further comprise a liquid nutrient solution. As used herein, the term "liquid nutrient solution" refers to a liquid which contains nutrients in the solution or in the mixture. The liquid nutrient solution is intended to comprise any liquid which enables plant growth. This includes oxygenated or aerated water mixtures which may or may not contain added nutrients.

In an aspect, a bioprotectant composition may further comprise at least one isolated micorrhyzal fungus, yeast or mold.

Microbial Cultures Inoculated with Isolated Microorganisms

Compositions of the present disclosure comprise cell-free supernatants of microbial cultures, and such cell-free supernatants may further comprise isolated microorganisms. Examples of these microorganisms include, but are not limited to, *Aspergillus* spp., *Bacillus* spp., *Rhodpseudomonas* spp., *Candida* spp., *Lactobacillus* spp., *Lactococcus* spp., *Pseudomonas* spp., *Saccharomyces* spp., or *Streptococcus* spp.; combinations thereof, or microbial consortia comprising one or more of these microorganisms. Examples of microorganisms which may be inoculated into a cell-free supernatant of the present invention include, but are not limited to, *Aspergillus* spp., for example, *Aspergillus* spp., for example, *Apergillus oryzae*, IN-AO1, deposited Sep. 4, 2014 with ATCC, PTA-121551; *Bacillus* spp., for example, *Bacillus subtilis*, IN-BSI, deposited Jan. 11, 2012 with ATCC, PTA-12385; *Rhodopseudomonas* spp., for example, *Rhodopseudomonas palustris*, IN-RPI, deposited Jan. 11, 2012 with ATCC, PTA-12387; *Rhodopseudomonas palustris*, IN-RP2, deposited Sep. 4, 2014 with ATCC, PTA-121533; *Candida* spp., for example, *Candida utilis*, IN-CU1, deposited Sep. 4, 2014 with ATCC, PTA-12550; *Lactobacillus* spp., for example, *Lactobacillus helveticus*, IN-LHI, deposited Jan. 11, 2012, PTA 12386; *Lactobacillus rhamnosus*, IN-LR1, deposited Sep. 4, 2014 with ATCC, PTA 121554; *Lactobacillus casei*, IN-LC1, deposited Sep. 4, 2014 with ATCC, PTA-121549; *Lactobacillus plantarum*, IN-LP1, deposited Sep. 4, 2014 with ATCC, PTA 121555; *Lactococcus* spp., for example, *Lactococcus lactis*, IN-LL1, deposited Sep. 4, 2014 with ATCC, PTA-121552; *Pseudomonas* spp., for example, *Pseudomonas aeuroginosa* or *Pseudomonas fluorescens; Saccharomyces* spp., for example, *Saccharomyces cerevisiae*, IN-SCI, deposited on Jan. 11, 2012 with ATCC, PTA-12384; or *Streptococcus* spp., for example, *Streptococcus lactis*; or combinations thereof, or a microbial consortia comprising one or more of the above, for example, IN-M1, deposited Jan. 11, 2012 with ATCC, PTA-12383, and/or IN-M2, deposited Sep. 4, 2014 with ATCC, PTA-121556. Such compositions comprising a cell-free supernatant further comprising microorganisms may be provided to a plant seed, to a plant fruit, to a plant, or to a plant at a particular growth stage, or combinations thereof, or to the soil or a plant growth media in which a plant, seed or plant part can be planted or grown, thereby providing bioprotection to the plant, seed, fruit or other plant parts.

The microbial cultures of the present disclosure may comprise differing amounts and combinations of these and other microorganisms depending on the methods being performed.

Microorganisms that are useful in compositions of the present disclosure, whether for microbial cultures that are the source for a cell-free supernatant composition or a cell-free supernatant culture further comprising microorganisms include, but are not limited to, one or more of the following in Table 1, Microorganisms

TABLE 1

| | |
|---|---|
| Lactobacillus | Hyperthermophile |
| Lactobacillus fermentum | Methanopyrus kandleri |
| Streptococcus thermophiles | Methanobrevibacter smithii |
| Lactococcus diacetyllactis | Pyrococcus furiosus |

TABLE 1-continued

| | |
|---|---|
| Lactococcus lactis | Ferrglobus |
| Bifidobacterium bifidum | Ferrglobus placidus |
| Lactibacillus delbruecki | Hydrothermal |
| Yeasts | Pyrolobus fumarii |
| Candida Antarctica | Thermophile |
| Candida chauliode | Sulfolobus acidocaldarius |
| Candida corydalis | Sulfolobus islandicus |
| Candida albicans | Sulfolobus metallicus |
| Lodderomyces elongisporus | Sulfolobus shibatae |
| Candida dosseyi | Sulfolobus solfataricus |
| Candida blattae | Bacillus thuringiensis |
| Candida ascalaphidarum | Bacillus thuringiensis Israelensis |
| Candida membranifaciens | Pseudomonas |
| Candida oleophila | Bradyrhizobia sp |
| Streptomyces albus | Pseudomonas alcaligenes |
| Lachancea fermentati, | Pseudomonas mendocina |
| Lachancea thermotolerans | Pseudomonas pseudoalcaligenes |
| Hanseniaspora vineae | Pseudomonas resinovorans |
| Saccharomycotina | Pseudomonas veronii |
| Aspergillus | Pseudomonas putida |
| Aspergillus oryzae | Pseudomonas stutzeri |
| Aspergillus niger | Pseudomonas fluorescens |
| Aspergillus terreus | Pseudomonas chlororaphis |
| Aspergillus fischerianus | Pseudomonas aurantiaca |
| Green sulfur bacteria | Pseudomonas aeruginosa, |
| Purple sulfur bacteria | White rot fungi |
| Chromatiaceae | Xanthomonas |
| Ectothiorhodospiraceae | Acinetobacter |
| Halothiobacillaceae | Rhodococcus sp. |
| Halothiobacillus halophilus | Arthrobacter |
| Halothiobacillus hydrothermalis | Aureobasidium sp. |
| Halothiobacillus kellyi | Alcaligeness sp. |
| Halothiobacillus neapolitanus | Leuconostoc sp. |
| Purple non sulfur bacteria | Sclerotium sp. |
| Rhodpseudomonas palustris | Clostridium, |
| Salt or Ocean Bacterium | Zymomonas |
| Halobacterium jilantaiense | Klebsiella |
| Halobacterium noricense | |
| Halobacterium salinarum | |
| Halobacterium piscisalsi | |

Bacteria which may be useful in compositions of the present disclosure, whether in microbial cultures that are the source for a cell-free supernatant composition or a cell-free supernatant culture further comprising microorganisms in the present disclosure include, but are not limited to, one or more of the following in Table 2.

TABLE 2

| |
|---|
| Bacillus alcalophilus |
| Bacillus alvei |
| Bacillus amyloliquefaciens |
| Bacillus aneurinolyticus |
| Bacillus aquaemaris |
| Bacillus brevis |
| Bacillus caldolyticus |
| Bacillus centrosporus |
| Bacillus cereus |
| Bacillus circulans |
| Bacillus clausii |
| Bacillus coagulans |
| Bacillus firmus |
| Bacillus flavothermus |
| Bacillus fusiformis |
| Bacillus globigii |
| Bacillus halodurans |
| Bacillus infernos |
| Bacillus larvae |
| Bacillus laterosporus |
| Bacillus lentus |
| Bacillus licheniformis |
| Bacillus megaterium |
| Bacillus mesentericus |
| Bacillus mucilaginosus |
| Bacillus mycoides |
| Bacillus natto |

TABLE 2-continued

*Bacillus pantothenticus*
*Bacillus polymyxa*
*Bacillus pseudoanthracis*
*Bacillus pumilus*
*Bacillus schlegelii*
*Bacillus sphaericus*
*Bacillus sporothermodurans*
*Bacillus stearothermophilus*
*Bacillus subtilis*
*Bacillus thermoglucosidasius*
*Bacillus thuringiensis*
*Bacillus vulgatis*
*Bacillus weihenstephanensis*

In various aspects, microorganisms grown for producing cell-free supernatant compositions of the present disclosure can be grown in fermentation, nutritive or culture broth in large, industrial scale quantities. For example, and not to be limiting, a method for growing microorganisms in 1000 liter batches comprises media comprising 50 liters of non-sulfur agricultural molasses, 3.75 liters wheat bran, 3.75 liters kelp, 3.75 liters bentonite clay, 1.25 liters fish emulsion (a commercially available organic soil amendment, from Nutrivert, Dunham, Quebec non-pasteurized), 1.25 liters soy flour, 675 mg. commercially available sea salt, 50 liters selected strains of microorganisms, up to 1000 liters non-chlorinated warm water. A method for growing the microorganisms can further comprise dissolving molasses in some of the warm water, adding the other ingredients to the fill tank, keeping the temperature at 30° C., and, after the pH drops to about 3.7 within 5 days, stirring lightly once per day and monitoring pH. The culture can incubate for 6 weeks or a predetermined time, the culture is then standardized (diluted or concentrated) to a concentration of $1\times10^5$-$1\times10^7$, or $1\times10^6$ cells/mL, after which the microorganisms are removed to result in a cell-free supernatant composition, a composition of the present disclosure.

A microbial culture, which is the source of a cell-free supernatant composition of the present disclosure can be inoculated with and comprise a combination of microorganisms from several genera and/or species. These microorganisms grow and live in a cooperative fashion, in that some genera or species may provide by-products or synthesized compounds that are beneficial to other microorganisms in the combination. For example, the microbial culture, which is the source of a cell-free supernatant composition of the present disclosure can be inoculated with and comprise both aerobic microorganisms, which need oxygen for metabolic activities, and anaerobic microorganisms, which use other sources of energy such as sunlight or the presence of specific substrates. This enables the microorganisms to colonize substrates in different regions of an environment.

A microbial culture, which is the source of a cell-free supernatant composition of the present disclosure can be inoculated with and comprise facultative microorganisms, for example, strains of *lactobacillus*, which modulate metabolic activities according to oxygen and/or nutrient concentrations in the environment.

Though not wishing to be bound by any particular theory, it is currently believed that microbial cultures, which are the sources of cell-free supernatant compositions disclosed in the present disclosure may, during fermentation (culture) produce metabolites that are reactive in a cooperative manner. For example, a substrate or enzyme excreted by one or more microorganisms may be acted on by excreted products from other microorganisms in the culture to form metabolites, which may be referred to as "tertiary metabolites."

These excreted products and those products formed from the interactions of excreted products may work in concert in a beneficial manner to enhance or induce bioprotective properties in plants.

All species of living organisms include individuals that vary genetically and biochemically from each other but are still within what is called the spectrum of normal variations within the species. These individual natural variations maybe the result of nondisruptive substitution or deletions in the gene sequence, variation in gene expression or RNA processing and/or variations in peptide synthesis and/or variation of cellular processing of intra cellular, membrane or secreted molecules. A microbial culture, which is the source of a cell-free supernatant composition of the present disclosure can be inoculated with microorganisms that are within or without the normal variations of a species. Identification of such microorganisms may be detected by genetic, molecular biological methods known to those skilled in the art, and/or by methods of biochemical testing.

For example, a microbial culture, which is the source of a cell-free supernatant composition of the present disclosure can be inoculated with and comprise microorganisms that were selected by isolating individual colonies of a particular microorganism. The colony members were characterized, for example, by testing enzyme levels present in the isolated microorganism and the activity with particular substrates in a panel of substrates, to establish an enzyme profile for the isolated microorganism.

Examples of these microorganisms that may be grown in cultures from which cell-free supernatants are derived include, but are not limited to, *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; combinations thereof, or microbial consortia comprising one or more of these microorganisms, including IN-M1, deposited Jan. 11, 2012 with ATCC, PTA-12383, and/or IN-M2, deposited Sep. 4, 2014 with ATCC, PTA-121556.

In an aspect, the *Aspergillus* spp. is *Aspergillus oryzae*. In an aspect, the *Aspergillus* spp. is *Aspergillus oryzae*, IN-AO1, deposited Sep. 4, 2014 with ATCC, PTA-121551.

In an aspect, the *Bacillus* spp. is *Bacillus subtilis*. In an aspect, the *Bacillus* spp. is *Bacillus subtilis*, referred to herein as IN-BS1, which was deposited with the ATCC under the Budapest Treaty, on Jan. 11, 2012, under Account No. 200139, and given Accession No. PTA-12385.

In an aspect, the *Rhodopseudomonas* spp. is *Rhodopseudomonas palustris*. In an aspect, the *Rhodopseudomonas* spp. is *Rhodopseudomonas palustris*, referred to herein as IN-RP1, which was deposited with the ATCC under the Budapest Treaty, on Jan. 11, 2012, under Account No. 200139, and given Accession No. PTA-12387. In an aspect, the *Rhodopseudomonas* spp. is *Rhodopseudomonas palustris*, IN-RP2, deposited Sep. 4, 2014 with ATCC, PTA-121533.

In an aspect, the *Candida* spp. is *Candida utilis*. In an aspect, the *Candida* spp. is *Candida utilis*, referred to herein as IN-CU1, deposited with the ATCC Patent Depository under the Budapest Treaty, on Sep. 4, 2014, with the designation IN-CU1, under Account No. 200139, with the ATCC Patent Deposit Designation No. PTA-121550.

In an aspect, the *Lactobacillus* spp. is *Lactobacillus caseii, Lactobacillus helveticus, Lactobacillus casei, Lactobaccillus rhamnosus*, or *Lactobacillus planterum*, or combinations thereof. In an aspect, the *Lactobacillus* spp. is *Lactobacillus helveticus*, IN-LHI, deposited Jan. 11, 2012, with ATCC and given Deposit No. PTA 12386.

In an aspect, the *Lactobacillus* spp. is *Lactobacillis casei*, referred to herein as IN-LC1, which was deposited with the ATCC Patent Depository under the Budapest Treaty, with the designation IN-LC1, on Sep. 4, 2014, under Account No. 200139, with the ATCC Patent Deposit Designation No. PTA-121549.

In an aspect, the *Lactobacillus* spp. is *Lactobacillus plantarum*, IN-LP1, deposited with the ATCC Patent Depository under the Budapest Treaty, on Sep. 4, 2014, with the designation IN-LP1, under Account No. 200139, with the ATCC Patent Deposit Designation No. PTA-121555.

In an aspect, the *Lactobacillus* spp. is *Lactobacillus rhamnosus*, IN-LR1, deposited with the ATCC Patent Depository under the Budapest Treaty, on Sep. 4, 2014, with the designation IN-LR1, under Account No. 200139, with the ATCC Patent Deposit Designation No. PTA-121554.

In an aspect, the *Lactobacillus* spp. is IN-LC1, IN-LL1, IN-LP1, IN-LR1, or combinations thereof.

In an aspect, the *Lactococcus* spp. is *Lactococcus lactis*, referred to herein as IN-LL1, which was deposited with the ATCC Patent Depository under the Budapest Treaty, with the designation IN-LL1, on Sep. 4, 2014, under Account No. 200139, with the ATCC Patent Deposit Designation No. PTA-121552.

In an aspect, the *Pseudomonas* spp. is *Pseudomonas aeruginosa*, or *Pseudomonas fluorescens*.

In an aspect, the *Rhodopseudomonas* spp. is *Rhodopseudomonas palustris*. In an aspect, the *Rhodopseudomonas* spp. is *Rhodopseudomonas palustris*, referred to herein as IN-RP1, which was deposited with the ATCC under the Budapest Treaty, on Jan. 11, 2012, under Account No. 200139, and given Accession No. PTA-12387. In an aspect, the *Rhodopseudomonas* spp. is *Rhodopseudomonas palustris*, IN-RP2, deposited with the ATCC Patent Depository under the Budapest Treaty, on Sep. 4, 2014, with the designation IN-RP2, under Account No. 200139, with the ATCC Patent Deposit Designation No. PTA-121553.

In an aspect, the *Saccharomyces* spp. is *Saccharomyces cerevisiae*. In an aspect, the *Saccharomyces* spp. is *Saccharomyces cerevisiae*, referred to herein as IN-SC1, which was deposited with the ATCC under the Budapest Treaty, on Jan. 11, 2012, under Account No. 200139, and given Accession No. PTA-12384.

In an aspect, the *Streptococcus* spp. is *Streptococcus lactis*.

In an aspect, a microbial consortia is IN-M1, deposited Jan. 11, 2012 with ATCC, PTA-12383. In an aspect, a microbial consortia is IN-M2, deposited Sep. 4, 2014 with ATCC, PTA-121556.

A composition of the present disclosure may comprise a cell-free supernatant from a fermentation culture comprising a mixture of isolated microorganisms comprising one or more of *Aspergillus oryzae, Bacillus subtilis*, referred to herein as IN-BS1 (Accession No. PTA-12385), *Rhodopseudomonas palustris*, referred to herein as IN-RP1 (Accession No. PTA-12387), *Candida utilis*, referred to herein as IN-CU1 (Accession No. PTA-121550), *Lactobacillus caseii*, referred to herein as IN-LC1 (Accession No. PTA-121549), *Lactobacillis helveticus, Lactobacillus lactis*, referred to herein as IN-LL1 (Accession No. PTA-121552), *Lactobacillus planterum*, referred to herein as IN-LP1 (Accession No. PTA-121555), *Lactobaccillus rhamnosus*, referred to herein as IN-LR1 (Accession No. PTA-121554), *Pseudomonas aeruginosa, Rhodopseudomonas palustris*, referred to herein as IN-RP1 (Accession No. PTA-12383), *Rhodopseudomonas palustris*, referred to herein as IN-RP2 (Accession No. PTA-121553), *Saccharomyces cerevisiae*, referred to herein as IN-SC1 (Accession No. PTA-12384), and *Streptococcus lactis*. Examples of isolated microorganisms inoculated in microbial cultures of the present disclosure include, but are not limited to, *Aspergillus oryzae, Rhodopseudomonas palustris, Candida utilis, Lactobacillus caseii, Lactobacillis helveticus, Lactobacillus casei, Lactobaccillus rhamnosus, Lactobacillus planterum, Pseudomonas aeruginosa, Rhodopseudomonas palustris, Saccharomyces cerevisiae*, and *Saccharomyces lactis*.

Compositions of the present disclosure may comprise differing amounts and combinations of these and other isolated microorganisms depending on the methods being performed. A microbial culture is formed by inoculating a microbial nutrient solution, commonly referred to as a broth, with one or more microorganisms disclosed herein. A microbial culture is formed by the growth and metabolic activities of the inoculated microorganisms. Thus, in various aspects, the microbial culture is inoculated with and comprises at least two of *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp. In an aspect, the microbial culture is inoculated with and comprises *Aspergillus oryzae, Bacillus subtilis, Lactobacillus helveticus, Lactobacillus casei, Rhodopseudomonas palustris*, and *Saccharomyces cervisiase*. In an aspect, the microbial culture is inoculated with and comprises a mixed culture, IN-M1 (Accession No. PTA-12383). In an aspect, the microbial culture is inoculated with and comprises *Aspergillus oryzae, Bacillus subtilis, Candida utilis, Lactobacillus casei, Lactobacillus helveticus, Lactobacillus plantarum, Lactobacillus rhamnosus, Lactococcus lactis, Rhodopseudomonas palustris*, and *Saccharomyces cervisiase*.

In an aspect, a microbial culture is inoculated with and comprises a mixed culture, the consortia IN-M1, deposited with the ATCC Patent Depository under the Budapest Treaty, on Jan. 11, 2012, under Account No. 200139, and given Accession No. PTA-12383. IN-M1 consortia comprises *Rhodopseudomonas palustris*, IN-RP1, ATCC Deposit No. PTA-12387; *Aspergillus oryzae, Saccharomyces cerevisiae*, IN-SC1, ATCC Deposit No. PTA-12384, *Bacillus subtilis*, IN-BSI, ATCC Deposit No. PTA-12385; *Lactobacillus helveticus*, IN-LH1, ATCC Deposit No. PTA-12386; and *Lactobacillus casei*. In an aspect, the microbial culture is inoculated with and comprises a mixed culture, IN-M1, in combination with one or more disclosed microbial organisms. After growth, the microbial culture is either diluted or concentrated to be $1\times10^5$-$1\times10^7$, or $1\times10^6$ cells/mL and a cell-free supernatant composition is derived from this IN-M1 fermentation culture by removing the microorganisms that were present in the microbial fermentation culture.

In an aspect, a microbial fermentation culture is inoculated with a mixed culture, IN-M2, deposited with the ATCC Patent Depository under the Budapest Treaty, on Sep. 4, 2014, with the designation IN-M2, under Account No. 200139, with the ATCC Patent Deposit Designation No. PTA-121556. The microbial consortia, IN-M2 comprises *Lactobacillus casei*, IN-LC1, ATCC Deposit No. PTA-121549; *Lactobacillus helveticus*, IN-LH1, ATCC Deposit No. PTA-12386; *Lactococcus lactis*, IN-LL1, ATCC Deposit No. PTA-121552; *Lactobaccillus rhamnosus*, IN-LR1m ATCC Deposit No. PTA-121554; *Lactobacillus planterum*, IN-LP1, ATTC Deposit No. PTA-12155; *Rhodopseudomonas palustris* IN-RPI, ATTC Deposit No. PTA-12387; *Rhodopseudomonas palustris*, IN-RP2, ATTC Deposit No. PTA-121553; *Saccharomyces cerevisiae*, IN-SC1, ATCC Deposit No. PTA-12384; *Candida utilis*, IN-CU1, ATCC Deposit No. PTA-121550; *Aspergillus oryzae*, IN-AO1, ATTC Deposit No. PTA-121551; and *Bacillus subtilis*, IN-BS1, ATCC Deposit No. PTA-12385. In an aspect, the microbial fermentation culture is inoculated with and comprises a mixed culture, IN-M2, in combination with one or more disclosed microbial organism. After growth, the microbial culture is either diluted or concentrated to be $1 \times 10^5$-$1 \times 10^7$, or $1 \times 10^6$ cells/mL and a cell-free supernatant composition is derived from this IN-M2 culture by removing the microorganisms that were present in the microbial culture.

Selection Criteria

One or more selection criteria enable the formulation of compositions of microorganisms that are cultured to provide a cell-free supernatant. For example, microorganisms that provide enzymes may be tested for enzyme activity levels for substrates and enzyme profile testing.

Methods for selection of a microorganism comprise testing for enzyme profile activity, growth characteristics under differing conditions such as oxygen or temperature, growth in particular media conditions, such as nitrates, carbohydrates, minerals or particular contaminants, and characteristic responses for particular microorganisms, such as the ability to form spores or the ability to grow in the presence of pollutants or contaminants. These tests allow for the characterization of a particular microorganism. Thus one testing criteria for microorganisms of the present disclosure is the interaction of the various species together. A microorganism may meet the enzyme profile tests and other criteria but it may not be able to grow well when added to a consortium of microorganisms used in a microbial culture to provide a cell-free supernatant composition.

Selection Criteria—Enzyme Profile Test

An example of an enzyme profile test comprises providing substrates and noting where there is high activity, +3 or greater, and where there is little to no activity, +2 and below. For example, a *lactobacillus* was tested and had a +5 enzyme level for alkaline phosphatase and a 0 for lipase. Such a *lactoballicus* may be admixed in a composition of the present disclosure with another microorganism where the lipase production is +4 or +5. Using microorganisms with differing strengths allows for cooperation among the microorganisms, completion of metabolic pathways in order not to have incomplete biochemical pathways which leave, either intermediary compounds that are not bioavailable to the other microorganisms, or are not available as nutrition or prebiotics, or that do not provide active compounds/enzymes. Incomplete biochemical pathways also do not provide molecules involved in the production or activation of nutritional elements for different species in the culture; hormones, growth factors, antibactericides, etc.

For example, bacterial strains isolated from *bacillus* species were characterized by enzyme profiles comprising ability to hydrolyze fibrous matter (cellulose and hemi cellulose), proteins and fat; and ability to complete the degradation of numerous intermediary molecules and cells that accumulate during the metabolic processes. On a scale of 0 to 5, by trained eyes in assessing the color change in the enzyme reaction, the ranking +4- to +5 are generally optimal, though lower responses by particular organisms may be acceptable.

The enzyme tests are commercially available and the testing procedures for microorganisms and methods for determining activity levels are well known in the art. Other characteristics include, for example, screening *Saccharomyces cerevisiae* for fermentation enzymes and *bacillus* species with known enzyme profiles. Testing microorganisms to determine which strains have high enzyme activity of certain enzymes which take part in proven fermentation pathways allows for identification of microorganisms that can use the available nutrients of organic origin. Isolation of individual colonies and the enzyme profile testing of these allows for the isolation of strong expressers of the enzymes.

Selection Criteria—Temperature

A selection criterion for microorganisms to be inoculated in a microbial culture used to make compositions of the present disclosure is growth of the microorganism at different temperatures. For example, one or more *Bacillus* strains were selected based on the ability to grow at different temperatures in aerobic conditions. Growth curves numbers of bacteria by OD and pH over time at different temperatures from 15 C-40° C. were used as the criteria for selection. Selected strains may be capable of growth in the presence of nitrates, capable of growth under anaerobic conditions or have other selected characteristics. For example, a *Bacillus* useful in methods and compositions of the present disclosure is characterized by the following: a +5 level of cellulase, a +2 to +3 level of proteinase, at least a +4 of fatase, grows in an 8% nitrate media, grows in a range of temperatures from 30° C. to 40° C., and does not form spores.

*B. subtilis* will grow anaerobically, either by using nitrate or nitrite as a terminal electron acceptor, or by fermentation. A two-component signal transduction system is an early stage in the regulatory pathway governing anaerobic respiration. One of the essential roles of ResD and ResE in anaerobic gene regulation is induction of fnr transcription upon oxygen limitation. FNR is a transcriptional activator for anaerobically induced genes, including those for respiratory nitrate reductase, narGHJI. *B. subtilis* has two distinct nitrate reductases, one for the assimilation of nitrate nitrogen and the other for nitrate respiration. In contrast, one nitrite reductase functions both in nitrite nitrogen assimilation and nitrite respiration. Unlike many anaerobes, which use pyruvate formate lyase, *B. subtilis* can carry out fermentation in the absence of external electron acceptors wherein pyruvate dehydrogenase is utilized to metabolize pyruvate. *B. subtilis* generally grows at 25-37° C., gene expression observed at 15° C.-40° C.

Selection Criteria—Oxygen Metabolism and Nutrient Concentrations

Selection criteria of oxygen metabolism and nutrient concentrations may be used to characterize microorganisms used to make a composition of the present disclosure. For example, *Lactobacillus* strains may be selected based on the ability to modulate metabolic activity depending on the oxygen concentration or nutrient concentration in the growth media, and by extension, what activities the lactobacilli will have in a particular environment when used in a composition of the present disclosure. For example, *Lactobacillus* converts lactose and other sugars to lactic acid. The production of lactic acid makes the *lactobacillus* environment acidic, which inhibits the growth of some harmful bacteria. The majority of acidifying flora in the culture generally control the pH of the culture. In certain *lactobacillus* strains, for example, *L. planterum*, the secretion of lactic acid is down regulated when the pH is below a pH 3 and up regulated when the pH is too high, whereas pH 4-5 is optimal.

Yeasts and Fungi

Beneficial yeasts, fungi and aspergillum provide nutrition, secreted enzymes and a network which provides filamentous structures in soil and which provide a structure to water or other liquids for biological components of a composition and the endogenous bacteria.

A characteristic for yeast or fungus that may be important in particular uses of compositions of the present disclosure is that they are nonpathogenic and nontoxic to humans and animals. It is known that mycelium in soil is important for aeration and that it excretes exoenzymes that breakdown organic nutritional sources for the fungi and that are used by the microbes in the environment. It is believed that the mycelium attract symbionts (*bacillus* sp., *pseudomonas* sp. etc) in the environment and provide a fibrous network to colonize in a coexistence and providing an exocellular cooperative source of nutrients.

Methods of Bioprotection

In an aspect, the present disclosure provides methods for bioprotection to a plant, such enhancing antimicrobial or antinematocidal responses of a plant, wherein a plant treated with a composition of the present disclosure shows less damage or pathology from a plant pathogen or pest compared to a similar control plant that was not treated with a composition of the present disclosure, that is exposed to the same plant pathogen or pest. A method comprises providing to a plant, seed, plant part, or soil or growth media of a plant a bioprotectant composition comprising a cell-free supernatant composition derived from a microbial culture inoculated with one or more isolated microorganisms, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp., or combinations thereof, or microbial consortia, for example, IN-M1, deposited Jan. 11, 2012 with ATCC, PTA-12383, and/or IN-M2, deposited Sep. 4, 2014 with ATCC, PTA-121556. The bioprotectant compositions disclosed herein may be provided to a plant seed, to a plant fruit, to a plant, plant part or to a plant at a particular growth stage, or combinations thereof, or to the soil or growth media of the plant, plant part or seed, thereby providing bioprotection to the plant such that the plant has less pathological damage from a microorganism or other plant pest than does a similar plant not treated with a composition of the present disclosure. Such methods are useful in protecting plants against a wide variety of pathogens including viruses, bacteria, and fungi. Exemplary pathogens include, but are not limited to, one or more of the following:

| Pathogen | Exemplary Hosts |
|---|---|
| *Erwinia cypripedii* | orchids, papaya, apple, pear, other Rosaceous crops, carrot, potato, tomato, leafy greens, squash, cucurbits, onion, green peppers |
| *Psuedomonas cypripedii* | orchids, carrot, potato, onion |
| *Alternaria solani* | infects stems, leaves and fruits of tomato, potato, eggplant, bell pepper, hot pepper, other members of the *Solanum* family |
| *Septoria lycopersici* | septoria leaf spot of tomato caused by the fungus *Septoria lycopersici* occurs on tomatoes worldwide; the fungus infects only solanaceous plants, |
| *Phytophthora infestans* | causes the serious potato disease known as late blight or potato blight. (Early blight, caused by *Alternaria solani*, is also often called "potato blight"). |
| *Gibberella zeae* | corn, soy |
| *Fusarium graminearum* | corn |
| *Vericillium* wilt | Potato |

In an aspect, disclosed methods may be useful in reducing the damage to plants, i.e., protecting plants (e.g., crop plants—soy, wheat, corn, canola) from one or more bacterial diseases. Exemplary bacteria include, but are not limited to, *Pseudomonas avenae*, *Xanthomonas campestris*, *Enterobacter dissolvens*, *Erwinia carotovora*, *Pseudomonas syringae*, *Clavibacter michiganensis*, *Pseudomonas syringae*, *Bacillus subtilis*, *Erwinia stewartii*, *Spiroplasma kunkelli*, *Pseudomonas amygdali*, *Curtobacterium flaccumfaciens*, and *Ralstonia solanacearum*.

In an aspect, disclosed methods may be useful in reducing the damage to plants, i.e., protecting plants, (e.g., crop plants—soy, wheat, corn, canola) from one or more fungal diseases. Exemplary fungi include, but are not limited to, *Colletotrichum graminicola*, *Aspergillus flavus*, *Rhizoctonia solani*, *Acremonium strictum*, *Lasiodiploda theobromae*, *Marasmiellus* sp., *Physoderma maydis*, *Acremonium strictum*, *Macrophomina phaseolina*, *Thanatephorus*, *Curvularia clavata*, *Didymella exitalis*, *Diplodia maydis*, *Stenocarpella macrospora*, *Sclerophthora rayssiae*, *Sclerophthora macrospora*, *Sclerospora graminicola*, *Peronosclerospora maydis*, *Peronosclerospora philippinensis*, *Peronosclerospora sorghi*, *Peronosclerospora spontanea*, *Peronosclerospora sacchari*, *Nigrospora oryzae*, *Alternaria alternate*, *Claviceps gigantean*, *Aureobasidium zeae*, *Fusarium subglutnans*, *Fusarium moiliforme*, *Fusarium avenaceum*, *Gibberella zeae*, *Botryosphaeria zeae*, *Cercospora sorghi*, *Exserohilum pedicellatum*, *Cladosporium cladosporioides*, *Hyalothyridium maydis*, *Cephalosporium maydis*, *Setsphaeria turcica*, *Cochliobolus carbonum*, *Penicillium* spp., *Phaeocytostroma ambiguum*, *Phaeosphaeria maydis*, *Botryosphaeria*, *Diplodia frument*, *Phoma terrestris*, *Phythium* spp., *Pythium aphanidermmatum*, *Epicoccum nigrum*, *Rhizoctonia zeae*, *Rhizoctonia solani*, *Setosphaeria rostrata*, *Puccinia sorghi*, *Puccinia polysora*, *Physopella pallescens*, *Sclerotium rolfsii*, *Bipolaris sorokiniana*, *Selenophoma* sp., *Gaeumannomyces graminis*, *Myrothecium gramineum*, *Monascus purpureus*, *Ustilago zeae*, *Ustilaginoidea vixens*, *Sphacelotheca reiliana*, *Cochliobolus heteroostrophus*, *Stenocarpella macrospora*, *Cercospora sorghi*, *Aspergillus* spp., *Phyllachora maydis*, *Trichoderma viride*, *Stenocarpella maydis*, *Ascochyta ischaemi*, *Alternaria* spp., *Colletotrichum truncatum*, *Arkoola nigra*, *Thielaviopsis basicola*, *Septoria glycines*, *Phialophora gregata*, *Macrophomina phaseolina*, *Choanephora infundibulifera*, *Pythium ultmum*, *Peronospora manshurica*, *Drechslera glycines*, *Cercospora sojina*, *Fusarium* spp., *Leptosphaerulina trifolii*, *Mycoleptodiscus terrestris*, *Neocosmospora vasinfecta*, *Phomopsis* spp., *Phytophtora sojae*, *Phymatotrichopsis omnivore*, *Diaporthe phaseolorum*, *Microsphaera diffusa*, *Cercospora kikuchi*, *Pyrenochaeta glycines*, *Pythium aphanidermatum*, *Cylindrocladium crotalariae*, *Dactuliochaeta glycines*, *Rhizoctonia solani*, *Phakopsora pachyrhizi*, *Spaceloma glycines*, *Sclerotinia sclerotiorum*, *Sclerotium rolfsii*, *Diaporthe phaseolorum*, *Stemphylium botryosum*, *Fusarium solani*, *Corynespora cassiicola*, *Nematospora coryli*, and *Cloeocercospora sorghi*.

In an aspect, disclosed methods may be useful in reducing the damage to plants, i.e., protecting plants (e.g., soy, wheat, corn, canola) from one or more parasitic nematodes. Exemplary parasitic nematodes include, but are not limited to, *Dolichodorus* spp., *Ditylenchus dipsaci*, *Radopholus similis*, *Heterodera avenae*, *Xiphinema* spp., *Nacobbus dorsalis*, *Hoplolaimus Columbus*, *Hoplolaimus* spp., *Pratylenchus* spp., *Longidorus* spp., *Circonemella* spp., *Meloidogyne* spp., *Helicotylenchus* spp., *Belonolaimus* spp., *Paratrichodorus* spp., *Tylenchorhynchus dubius*, *Paratylenchus projectus*, *Rotylenchulus reniformis*, *Criconemella ornate*, *Meloid-* ogyne arenaria, Hemicycliophora spp., Heterodera glycines, Belonolainus gracilis, Paratrichodorus minor, and Quinisulcius acutus.

Bioprotection, such as enhanced antimicrobial or antinematocidal activity or reduction of damage to plants from pathogens or pests, provided to plants by compositions disclosed herein, may be useful at a variety of different stages. For example, enhanced antimicrobial activity may be useful in the management of and/or protection (of seed tubers such as potatoes) from fungal infections and molds in storage. Without treatment with compositions disclosed herein, these fungi and molds may be directly transported with the seeds or transported with the seeds to the soil upon planting. Additional examples of relevant applications include, but are not limited to, in the management of bacterial infections (e.g., brown rot or *erwinia*) or algae in storage and/or at planting, in the protection of seed tubers (e.g., potatoes) from bacterial infections (e.g., brown rot or *erwinia*) or algae in storage and/or at planting, in the treatment of pieces of seed tubers (e.g., potatoes) before and when planting, and in the treatment of soil and/or irrigation water in fields or greenhouses for common plant pathogens endemic in the growing environment (e.g., human infection management coliform or *enterobacter, salmonella*, etc.).

Methods of Bioprotection—Decreasing Abiotic Stress

In an aspect, the disclosure provides methods of reducing abiotic stress in plants, wherein a plant treated with a composition of the present disclosure shows less abiotic stress compared to a similar control plant that was not treated with a composition of the present disclosure, that is exposed to the abiotic stress. A method comprises providing a bioprotectant composition comprising a cell-free supernatant composition derived from of a microbial culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof, or microbial consortia, for example, IN-M1, deposited Jan. 11, 2012 with ATCC, PTA-12383, and/or IN-M2, deposited Sep. 4, 2014 with ATCC, PTA-121556. The bioprotectant compositions disclosed herein may be provided to a plant seed, to a plant fruit, to a plant, or to a plant at a particular growth stage, or combinations thereof, thereby reducing abiotic stress in the treated plant compared to a similar plant that is not treated with a composition disclosed herein. Abiotic stress is defined as environmental conditions that reduce growth and yield below optimum levels. It has been reported that abiotic stress may cause the largest crop loss of any other factor, reducing the yield of most major crops by in excess of 50% from their potential yield (Wang W (2007) *Planta* 218: 1-14). Indeed, these abiotic stresses may increase in the near future due to global climate change. Examples of abiotic stress include, but are not limited to, drought, flood, extreme temperatures, high wind, wildfires, rock content, pH, high radiation, heavy metal uptake, salt uptake, and rapid rehydration during seed germination.

In various aspects, disclosed bioprotectant compositions may provide simultaneous protection against both abiotic and biotic stresses. This dual modality has been previously demonstrated in certain bacteria. For example, *P. fluorescens* TDK1, *Pseudomonas putida* UW4, *Bacillus* sp., and *Arthrobacter* sp. have been shown to enhance resistance against various soil-borne pathogens, and also mitigate salt, as well as drought, stress in different plants (Mayak et al. (2004) *Plant Physiology and Biochemistry* 42: 565-572; Mayak et al. (2004) *Plant Science* 166: 525-530; Haas and Defago (2005) *Nature Reviews Microbiology* 3: 307-319; Saravanakumar and Samiyappan (2007) *Journal of Applied Microbiology* 102: 1283-1292; Barriuso et al. (2008) *Plant Biotechnology Journal* 6: 442-452).

Methods of Applying a Composition

Disclosed compositions can be used in methods to treat a wide variety of plants and/or seeds, or treat soil or growth media of plants, plant parts or seeds. The plants treated can be dicots or monocots. Exemplary plants include, but are not limited to, alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Exemplary ornamental plants include, but are not limited to, *Arabidopsis thaliana*, Saintpaulia, *petunia, pelargonium*, poinsettia, *chrysanthemum*, carnation, *zinnia*, and turfgrasses.

Preventative Applications

In an aspect, disclosed bioprotectant compositions can be applied at any particular time, or one or more times, in the plant growth cycle, such as a time prior to infection with a plant pathogen. Suitable application methods include, but are not limited to, high or low pressure spraying, drenching, coating, immersion, and injection. In various aspects, disclosed compositions can be applied to soil or other plant grow media and/or can be applied to seeds prior to or during planting. When treating seeds, disclosed compositions can be applied by a variety of techniques including, but not limited to, high or low pressure spraying, coating, immersion, and injection. Once treated, seeds can be planted in natural or artificial soil and cultivated using conventional procedures to produce plants. After plants have propagated from seeds treated in accordance with the present disclosure, the plants may be treated with one or more applications of disclosed compositions.

In an aspect, disclosed bioprotectant compositions can be applied to the seedlings prior to or during transplantation.

In an aspect, disclosed bioprotectant compositions can be applied to all or part of the plant. For example, a disclosed bioprotectant composition can be applied to the stems, roots, leaves, plant products (e.g., grain, fruit, forage, crop debris, etc.), and/or propagules (e.g., cuttings). The plant may be treated at one or more developmental stages. For example, the plant may be treated at the vegetative stage, the early reproductive stage, the flowering stage, and/or the late reproductive stage.

Curative Applications

In an aspect, disclosed bioprotectant compositions can be applied subsequent to infection with a plant pathogen. Suitable application methods include, but are not limited to, high or low pressure spraying, drenching, coating, immersion, and injection. In various aspects, disclosed compositions can be applied to the soil or can be applied to the seeds prior to or during planting. When treating seeds, disclosed compositions can be applied by a variety of techniques including, but not limited to, high or low pressure spraying, coating, immersion, and injection. Once treated, the seeds can be planted in natural or artificial soil and cultivated using conventional procedures to produce plants. After plants have propagated from seeds treated in accordance with the present disclosure, the plants may be treated with one or more applications of disclosed compositions.

In an aspect, disclosed bioprotectant compositions can be applied to the seedlings prior to or during transplantation.

In an aspect, disclosed bioprotectant compositions can be applied to all or part of the plant. For example, disclosed composition can be applied to the stems, roots, leaves, plant products (e.g., grain, fruit, forage, crop debris, etc.), and/or propagules (e.g., cuttings). The plant may be treated at one or more developmental stages. For example, the plant may be treated at one or more of the vegetative stage, the early reproductive stage, the flowering stage, and/or the late reproductive stage, or combinations thereof.

Alternative Applications

In an aspect, disclosed bioprotectant compositions can be applied to a delivery vehicle, wherein the delivery vehicle serves as a means of transporting the bioprotective properties from the delivery vehicle to the soil, plant, seed, field, etc. For example, disclosed compositions can be applied to a delivery vehicle (e.g., a particle, a polymer, or a substrate) to be used in filtration systems for the treatment of irrigation water. This technique may be useful in a variety of plant environments such as fields, greenhouse facilities, vertical farms, urban greening systems, and hydroponic systems. In an aspect, disclosed compositions can be applied to a polymer as a wetting agent and/or gel that releases water as needed. In an aspect, disclosed compositions can be applied to a delivery system for actives that effect solubility to concentrate actives for seed coatings. As used herein, "actives," refers to a molecule, or combination of molecules, having desired bioprotective properties that are produced during fermentation. Exemplary actives include, but are not limited to, acetic acid; butyric acid; proprionic acid; 3-hydroxydecanoic acid; 3-hyroxydodecanoic acid; 3-hydroxy tetradecanoic acid; 3-hydroxy-5-cis-dodecenoic acid, or combinations thereof. It is understood that in various aspects, fermentation refers to a culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof. Actives can be isolated or concentrated from the cell-free supernatant of a culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof, or a microbial consortia, for example, IN-M1, deposited Jan. 11, 2012 with ATCC, PTA-12383, and/or IN-M2, deposited Sep. 4, 2014 with ATCC, PTA-121556.

In an aspect, disclosed compositions can be applied to a delivery system for actives that allow the broadcasting of small quantities of actives on a larger area. Additional vehicles for the application of disclosed compositions include, but are not limited to, growing media, soil, mineral wood, and wolf track systems. Disclosed compositions, in an effective amount, can be added to water or other liquid solutions provided to plants. Disclosed compositions, in an effective amount, can be added to soil or other materials used for growing plants (growing media), and can be reapplied one or more times after seeds are planted or plants are transplanted to the growing media.

Methods of Making an Article

In one aspect, the invention relates to methods of making an article comprising a cell-free supernatant comprising providing disclosed cell-free supernatant composition to a surface of an article. The method may comprise steps comprising drying the cell-free supernatant composition on a surface to attach the cell-free supernatant composition to the surface. A method may comprise pre-treating a surface to aid in attachment of the cell-free supernatant composition. A method may comprise adding one or more components to the cell-free supernatant composition to aid in its attachment to the surface. A method may comprise adding one or more components to both the cell-free supernatant composition and the surface to aid in attachment of the cell-free supernatant composition to the surface. Such components may be any material, compound or molecule that aids in the attachment of the cell-free supernatant composition to the surface or the article. For example, glues, starches, natural materials, polymeric materials and materials that are known for attaching solutions to surfaces or articles. A method may comprise surfaces or articles wherein the surface or article is a glass bead, inert materials, woven materials, nonwoven materials, natural materials such as plant material, coco mats, silica beads, polymeric materials, plant container, container, filter structures, porous inert particles, or zeolites. Articles made with attached cell-free supernatant compositions of the present disclosure are contemplated by the invention and may be comprised in the term cell-free supernatant composition.

In an aspect, the article comprises a biofilm. In a further aspect, the biofilm is a biofilm prepared by using a culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof, or a microbial consortia, for example, IN-M1, deposited Jan. 11, 2012 with ATCC, PTA-12383, and/or IN-M2, deposited Sep. 4, 2014 with ATCC, PTA-121556. In a still further aspect, the biofilm is prepared using a culture inoculated with one or more biofilm-producing microorganisms that selected for the property of producing a biofilm. In an aspect, the method of producing the article comprises a step of producing the biofilm using one or more biofilm-producing microorganisms, and in a another step, the biofilm is infiltrated with a culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof, or a microbial consortia, for example, IN-M1, deposited Jan. 11, 2012 with ATCC, PTA-12383, and/or IN-M2, deposited Sep. 4, 2014 with ATCC, PTA-121556, and/or a cell-free supernatant prepared from a culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof, or a microbial consortia, for example, IN-M1, deposited Jan. 11, 2012 with ATCC, PTA-12383, and/or IN-M2, deposited Sep. 4, 2014 with ATCC, PTA-121556.

In an aspect, the method further comprises drying the article after providing the cell-free supernatant.

In an aspect, the method comprises the step of treating the surface of the article prior to providing the cell-free supernatant to the surface of the article.

In an aspect, the method further comprises the step of treating the surface of the article after providing the cell-free supernatant to the surface of the article.

In an aspect, providing the cell-free supernatant composition comprises spraying. In an aspect, providing the cell-free supernatant composition comprises immersion of the article in vessel containing a cell-free supernatant composition.

In an aspect, the method comprises adding one or more surface-attachment aids to the cell-free supernatant composition, wherein the surface-attachment aid facilitates the attachment one or more components of the cell-free supernatant to the surface of the article. In an aspect, the surface-attachment aid is capable of linking the one or more components in the cell-free supernatant to the surface of the article. In an aspect, the surface-attachment aid is a chemical compound. In an aspect, the chemical compound provides a reversible chemical linkage between one or more components of the cell-free supernatant to the surface of the article. In an aspect, the chemical compound provides an irreversible chemical linkage between one or more components of the cell-free supernatant to the surface of the article. In an aspect, the surface-attachment aid is a nucleic acid, a protein, an oligonucleotide, or a peptide.

In an aspect, the article is a biochar, a bead, a filter, a container, a nanoparticle, a microparticle, a mat, a screen, a powder, a particulate, or a cloth. In an aspect, the article comprises a woven material, a non-woven material, a plant material, a mat, a container, a polymeric material, a porous material, a non-porous material, or a zeolite.

Methods of Preparing a Cell-Free Supernatant Composition

In an aspect, the disclosure provides methods of preparing a cell-free supernatant composition comprising the steps of: (a) inoculating a fermentation broth (a microbial nutritive media) with an isolated microorganism, wherein the microorganism comprises *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp., or combinations thereof, or a microbial consortia, for example, IN-M1, deposited Jan. 11, 2012 with ATCC, PTA-12383, and/or IN-M2, deposited Sep. 4, 2014 with ATCC, PTA-121556, to form a microbial culture; (b) incubating the microbial culture for at least five hours; and standardizing the number of microorganisms per ML, for example, $1\times10^5$-$1\times10^7$, or $1\times10^6$ cells/mL; (c) centrifuging the culture after step (b) for at least 10 minutes at a centrifugal force of 10,000×g; wherein the liquid portion, separated from the packed cells, is a cell-free supernatant composition. The method may comprise measuring characteristics of the microbial culture. Measuring characteristics of the microbial culture may comprise measuring the predation of one or more selected microorganism by one or more other selected microorganisms, measuring factors or proteins released or made by one or more microorganisms, pH changes, or extracellular enzymes excreted by one or more selected microorganisms and its effects on one or more other selected microorganism, measuring the number of cells per mL of one or more selected microorganism in the mixture, determining growth rate for one or more selected microorganisms, or combinations of characteristics and measurements. The method may comprise using the measured characteristics of the microbial culture to determine if one or more microorganisms are to be removed from the incubation mixture or if one or more microorganisms are to be added to the microbial culture. The method may comprise determining if one or more microorganisms are to be removed from the microbial culture, wherein the method may comprise killing the microbial culture and repeating the steps to make a new microbial culture without the identified unwanted microorganism. The method may comprise steps wherein when one or more microorganisms are to be added to the microbial culture, the method may comprise adding one or more desired isolated microorganisms to the microbial culture, and growing the microbial culture to a predetermined cellular concentration to produce a mature microbial culture. The method may comprise repeating the steps of the method one or more times. The method may comprise growing the cells of the microbial culture to a particular concentration to form an individual microbial culture. The method may comprise making one or more microbial culture and f) combining the individual microbial cultures to form a mixed microbial culture. The method may comprise growing the mixed microbial culture to a particular concentration. The method may comprise growing the mixed microbial culture to form an mixed microbial culture and measuring characteristics of the mixed microbial culture. The method may comprise steps of measuring characteristics of the mixed microbial culture comprises measuring the predation of one or more selected microorganism by one or more other selected microorganisms, measuring factors, pH changes, or extracellular enzymes excreted by one or more selected microorganisms and its effects on one or more other selected microorganism, measuring the number of cells per mL of one or more selected microorganism in the mixture, determine growth rate for one or more selected microorganisms, or combinations of measurements. The method may comprise using the measured characteristics of the mixed microbial culture to determine if one or more microorganisms is to be removed from the incubation mixed culture or if one or more microorganisms is to be added to the mixed microbial culture, or if no change in microorganisms is to be made. The method may comprise steps for when one or more microorganisms are to be removed from the incubation mixed culture, the method further comprises killing the mixed microbial culture; and repeating the steps to make a new mixed microbial culture without the undesired one or more microorganisms. The method may comprise repeating steps of the method one or more times. The method may comprise steps wherein when one or more microorganisms are added to the mixed microbial culture, the method further adding one or more isolated microorganisms to the mixed microbial culture, and growing the mixed microbial culture to a predetermined cellular concentration to produce a mixed microbial culture. Once the microbial culture has reached the desired stage, such as time of incubation or density of cell growth, the supernatant is removed from the cells. This can be accomplished by any method known to those in the art for removing cells from a liquid, including but not limited to centrifugation or filtration. The resulting cell-free supernatant is a bioprotectant composition of the present disclosure. The supernatant may or may not be sterilized.

In an aspect, a method comprises the step of sterilizing the cell-free supernatant.

In an aspect, sterilizing is filter sterilization.

In an aspect, a method comprises incubating the microbial culture (inoculated fermentation broth) for at least 24 hours. In an aspect, a method comprises incubating the microbial culture (inoculated fermentation broth) for at least 60 hours. In an aspect, a method comprises incubating the microbial culture (inoculated fermentation broth) for at least 120 hours. In an aspect, a method comprises incubating the microbial culture (inoculated fermentation broth) for at least 360 hours.

Methods and compositions for bioprotection, including, but not limited to, reducing pathological symptoms and disease in plants from plant pathogens and reducing abiotic stress, are disclosed herein. For example, a method for reducing plant pathological damage due to a plant pathogen comprises contacting a plant, plant part, seed, soil or a plant growth media with a bioprotectant composition comprising a cell-free supernatant of a microbial fermentation culture inoculated with IN-M1, deposited under ATCC Accession No. PTA-12383, or IN-M2, deposited under ATCC Accession No. PTA-121556, wherein a plant, plant part, seed, soil or a plant growth media treated with the bioprotectant composition has reduced pathological damage in the plant compared to an untreated control plant under the same conditions. A method for reducing abiotic stress of a plant comprising, contacting a plant, plant part, seed, soil or a plant growth media with a bioprotectant composition comprising a cell-free supernatant of a microbial fermentation culture inoculated with IN-M1, deposited under ATCC Accession No. PTA-12383, or IN-M2, deposited under ATCC Accession No. PTA-121556, wherein a plant, plant part, seed, soil or a plant growth media treated with the bioprotectant composition has reduced abiotic stress in the plant compared to an untreated control plant under the same conditions.

A bioprotectant composition may further comprise an herbicide, a pesticide, a nematocide, a fungicide, a fertilizer, or a nutrient component, or combinations thereof. A microbial culture comprises humic acid, potato starch, or molasses. A bioprotectant composition may further comprise a wetting agent, a gelling agent, a higher fatty acid, 3-hydroxydecanoic acid, 3-hydroxydodecanoic acid, 3-hydroxytetradecanoic acid, 3-hydroxy-5-cis-dodecenoic acid, a volatile fatty acid, acetic acid, butyric acid, isobutyric acid, propionic acid, or combinations thereof. The pH of the bioprotectant composition is from pH 5.0 to 7.0. Plants useful in the methods may comprise any food or ornamental plants, trees or grasses. For example, a plant may be rice, wheat, corn, tomato, banana, coffee, soybean, potato, a citrus, orange, grapefruit, lemon, lime, cucumber, cauliflower, or strawberry, a vegetable plant, an ornamental plant or a tree. Contacting a plant with a bioprotectant composition comprises contacting plant parts, seeds, roots, shoots, tubers, leaves or stalks of plants. Contacting with a bioprotectant composition may comprise contacting soil or growth media of plants.

Plants may be grown under hydroponic conditions, aeroponic conditions or combined aeroponic and hydroponic conditions. Plants may be grown in a greenhouse or in a field. Seeds may be contacted with a bioprotectant composition prior to planting the seeds or prior to storage of the seeds. A plant may be contacted with the bioprotectant composition during transplantation of the plant, during the plant's vegetative stage, at the plant's flowering stage, at the plant's reproductive stage, or combinations thereof. A plant may be contacted with a bioprotectant compositions one or more times during its lifespan. A plant may be contacted with a bioprotectant composition following the plant's contact (such as infection) by a microbial plant pathogen. A plant may be contacted with a bioprotectant composition following contact by a nematode. A plant may be contacted with a bioprotectant composition before contact by a microbial plant pathogen or a nematode. A plant, plant part, seed, soil or a plant growth media may be contacted with a bioprotectant composition by providing the bioprotectant composition admixed with irrigation water, by spraying the bioprotectant composition onto the plant, plant part, seed, soil or a plant growth media, or by other known methods for contacting plants The plant, plant part, seed, soil or a plant growth media may be contacted by an article comprising a bioprotectant composition. An article may be a biochar, a bead, a filter, a container, a nanoparticle, a microparticle, a mat, a screen, a powder, a particulate, or a cloth to which a bioprotectant composition is dried or adhered. An article may be a woven material, a non-woven material, a plant material, a mat, a container, a polymeric material, a porous material, a non-porous material, or a zeolite to which a bioprotectant composition is dried or adhered.

EXAMPLES

Example 1 A Method for Making a Microbial Culture for Preparation of a Cell-Free Supernatant A microorganism, such as a bacteria or yeast, was selected for inclusion in the composition, based on its enzyme activity profile, its ability to grow in media, its lack of spore formation, or other criteria described herein. The microorganism was grown in standard medium for that organism and when at an exponential growth phase, was aliquoted and stored. The media for growing microorganisms, such as yeasts and bacteria, are known to those skilled in the art.

For example, in making I-M Lab, an aliquot (5 mL of cells at $1 \times 10^6$) of each of IN-LH1, IN-BS1 and *L. casei* (IN-LC1) were added to a media suitable for lactobacilli and *bacillus*, such as water (700 mL), molasses (37.5 g), bentonite clay (3.75 g), and sea salt (3.75 g). The bacteria were grown to an optical density of 0.752 determined at 600 nm (hereinafter, "$OD_{600}$").

In making I-M PNSB, an aliquot (5 mL of cells at $1 \times 10^6$) of IN-RPI was added to a media suitable for phototrophic bacteria. For example, water (134 mL), fish emulsion (9 mL), and IN-SCI culture ($1 \times 10^6$ cells, 1 mL) were combined, and then the volume was adjusted to 144 mL with water and the cells were grown to an $OD_{600}$ 0.856. A carbohydrate source (i.e., molasses) can also be added. The fish emulsion used herein is commercially available as an organic soil amendment from Nutrivert, Dunham, Quebec (non-pasteurized).

In making I-M Yeast, an aliquot (5 mL of cells at $1 \times 10^6$) of IN-SC1 and *A. oryzae* (IN-AO1) ($OD_{600}$ 0.3) were added to a media suitable for yeast, such as water (390 mL), molasses (1 g), fish emulsion (29 g), kelp (9 g), and wheat germ (1 g) were combined, and the volume was adjusted to 432 ml with water and the yeast were grown to an $OD_{600}$ 0.574.

To make microbial cultures, comprising microorganisms such as IN-M1 deposited with ATCC Patent Deposit Designation No. PTA-12383, the three microbial cultures were used. I-M Lab, I-M PNSB and I-M Yeast were added to a medium comprising water, molasses, mineral powder, sea salt, and wheat bran as shown below. The three microbial component mixtures were added in the percentages shown in Table 1 below.

TABLE 1

| Components of Composition | % |
|---|---|
| WATER | 89.70 |
| MOLASSES | 5.00 |
| I-M LAB | 2.00 |
| I-M PNSB | 2.00 |
| I-M YEAST | 1.00 |
| Bentonite clay (Utah) | 0.10 |
| SEA SALT (commercially available) | 0.10 |
| WHEAT BRAN | 0.10 |
| TOTAL | 100 |

The molasses, sea salt, wheat bran and mineral powder were dissolved in some of the warm water and the temperature was kept at 45-50° C. The I-M LAB, the I-M PNSB and I-M Yeast were added together into a separate container and blended. The total was 50 L, of which 20 L was I-M LAB, 20 L was I-M PNSB, and 10 L was I-M Yeast (the composition comprising these three microbial compositions may be referred to herein as a seed culture). This seed culture was added to the main tank of media and water was added to make 1000 L, and the temperature was kept at 37° C. with light agitation until the pH is pH 4.0 and below.

The seed culture for IN-M1 (an initial mixed culture) comprised IN-RP1, ATCC Deposit No. PTA-12387; IN-BS1, ATCC Deposit No. PTA-12385; IN-SC1, ATCC Deposit No. PTA-12384; IN-AO1, IN-LH1, ATCC Deposit No. PTA-12386; and IN-LC1 was made under sterile conditions and used in one or more of the following secondary fermentation cultures.

IN-M2 seed culture was made in a similar manner. Starting with a *Lactobacillus/Lactococcus* initial culture of I-M2 Lab, an aliquot (5 mL of cells at $1 \times 10^6$) of each of IN-LH1 (*L. helviticus*), ATCC Deposit No. PTA-12386; IN-LP1 (*L. plantarum*), ATTC Deposit No. PTA-12155; IN-LC1 (*L. casei*), ATCC Deposit No. PTA-121549; IN-LR1 (*L. rhamnosus*) ATCC Deposit No. PTA-121554; and IN-LL1 (*L. lactis*) ATCC Deposit No. PTA-121552; were added to a media suitable for lactobacilli and *lactococcus*, such as water (700 mL), molasses (37.5 g), bentonite clay (3.75 g), and sea salt (3.75 g). The bacteria were grown to an optical density of 0.752 determined at 600 nm (hereinafter, "$OD_{600}$").

In making I-M2 PNSB, an aliquot (5 mL of cells at $1 \times 10^6$) of IN-RPI (*Rhodopseudomonas palustris*) and IN-RP2 (*Rhodopseudomonas palustris*) was added to a media suitable for phototrophic bacteria. For example, water (134 mL), fish emulsion (9 mL), and IN-SCI culture ($1 \times 10^6$ cells, 1 mL) were combined, and then the volume was adjusted to 144 mL with water and the cells were grown to an $OD_{600}$ 0.856. A carbohydrate source (i.e., molasses) can also be added. The fish emulsion used herein is commercially available as an organic soil amendment from Nutrivert, Dunham, Quebec (non-pasteurized).

In making I-M2 Yeast, an aliquot (5 mL of cells at $1 \times 10^6$) of IN-SC1 (*Saccharomyces cerevisiae*), IN-CU1 (*Candida utilis*) and IN-AO1 (*A. oryzae*, ATTC Deposit No. PTA-121551) ($OD_{600}$ 0.3) were added to a media suitable for yeast, such as water (390 mL), molasses (1 g), fish emulsion (29 g), kelp (9 g), and wheat germ (1 g) were combined, and the volume was adjusted to 432 ml with water and the yeast were grown to an $OD_{600}$ 0.574.

In making I-M2 *Bacillus*, IN-BS1 (*Bacillus subtilis*) was added to a media suitable for *bacillus*, such as water (700 mL), molasses (37.5 g), bentonite clay (3.75 g), and sea salt (3.75 g). The bacteria were grown to an optical density of 0.752 determined at 600 nm (hereinafter, "$OD_{600}$").

To make microbial cultures, comprising microorganisms such as IN-M2 deposited with ATCC Deposit No. PTA-121556, the four microbial cultures were used. I-M2 Lab, I-M2 PNS, I-M2 Yeast and IN-M2 *Bacillus* were added to a medium comprising water, molasses, mineral powder, sea salt, and wheat bran as shown below. The four microbial component mixtures were added in the percentages shown in Table 1 below.

TABLE 1

| Components of Composition IN-M2 | % |
| --- | --- |
| WATER | 87.70 |
| MOLASSES | 5.00 |
| I-M2 LAB | 2.00 |
| I-M2 PNSB | 2.00 |
| I-M2 YEAST | 1.00 |
| I-M2 *BACCILUS* | 2.00 |
| Bentonite clay (Utah) | 0.10 |
| SEA SALT (commercially available) | 0.10 |
| WHEAT BRAN | 0.10 |
| TOTAL | 100 |

The molasses, sea salt, wheat bran and mineral powder were dissolved in some of the warm water and the temperature was kept at 45-50° C. The I-M2 LAB, the I-M2 PNSB, I-M2 Yeast and I-M2 *Bacillus* were added together into a separate container and blended. The total was 70 L, of which 20 L was I-M2 LAB, 20 L was I-M2 PNSB, 20 L was I-M2-*Bacillus* and 10 L was I-M Yeast (the composition comprising the four microbial compositions may be referred to herein as a seed culture). This seed culture was added to the main tank of media and water was added to make 1000 L, and the temperature was kept at 37° C. with light agitation until the pH is pH 4.0 and below.

Alternate 1

A secondary fermentation culture (a mixed culture) was made from the above seed culture of IN-M1 or IN-M2 to produce a stable concentrated culture (mixed microbial culture) comprising approx. 1 billion microorganisms per liter ($1 \times 10^6$ cells/mL), from which a cell-free supernatant composition is made by removing the microorganisms present. A typical 1000 liter secondary fermentation batch, was inoculated with 50 litres of the seed culture (described above—20 L was I-M LAB, 20 L was I-M PNSB, and 10 L was I-M Yeast) and the media was 50-200 liters of non-sulphur agricultural molasses, 3.75 liters wheat bran, (0.02-0.05% by volume), 3.75 liters kelp, (0.02-0.05% by volume), 3.75 liters bentonite clay, (0.02-0.05% by volume), 1.25 liters fish emulsion (a commercially available organic soil amendment, from Nutrivert, Dunham, Quebec non-pasteurized, 1.25 liters soy flour, (0.005-0.03% by volume), 675 mg commercially available sea salt, and enough non-chlorinated warm water to make 1000 L.

The pH dropped to about 3.7 by Day 5 after inoculation, and the culture was grown and stirred lightly once per day and pH was monitored. The culture was incubated for 3-10 weeks at 26-33° C. The pH of the final product was adjusted to pH 5 or pH 7 depending on the intended use of the protectant. This resulting composition may be referred to as a concentrated composition, with cells at $1 \times 10^6$ cells/mL. A cell-free supernatant composition was made by removing the cells from the concentrated composition, IN-M1 CFS or IN-M2 CFS. Cells were removed by any method known to those of skill in the art, such as by filtering or centrifugation.

Alternatively, the foregoing method was modified with regard in the second fermentation such that tryptone or potato extract replaced molasses in the culture medium. Briefly, 30-50 liters of the primary fermentation (in medium comprising molasses) prepared using IN-M1 or IN-M2 consortia was used to inoculate the second fermentation (1000 liters) containing 0.5-2% bacto tryptone or potato extract. This modification is described in greater detail immediately below.

Alternate 2

A secondary fermentation culture (a mixed culture) was made from the above seed culture of IN-M1 or IN-M2 to produce a stable concentrated culture (mixed microbial culture) comprising approx. 1 billion microorganisms per liter ($1\times10^6$ cells/mL)), from which a cell-free supernatant composition is made by removing the microorganisms present. A typical 1000 liter secondary fermentation batch, was inoculated with 30-50 litres of the In-M1 or In-M2 seed culture and the secondary culture media contained 0.5-2% bacto tryptone, 0.25-1% yeast extract and 0.3-0.7 gm/liter $CaCl_2$ 3.75 liters wheat bran, (0.02-0.05% by volume), 3.75 liters kelp, (0.02-0.05% by volume), 3.75 liters bentonite clay, (0.02-0.05% by volume), 1.25 liters fish emulsion (a commercially available organic soil amendment, from Nutrivert, Dunham, Quebec non-pasteurized, 1.25 liters soy flour, (0.005-0.03% by volume), 675 mg commercially available sea salt, and enough non-chlorinated warm water to make 1000 L.

The pH dropped to about 3.7 by Day 5 after inoculation, and the culture was grown and stirred lightly once per day and pH was monitored. The culture was incubated for 3-10 weeks at 26-33° C. The pH of the final product was adjusted to pH 5 and pH 7, depending on the intended use of the protectant. This resulting composition may be referred to as a concentrated composition, with cells at $1\times10^6$ cells/mL. A cell-free supernatant composition was made by removing the cells from the concentrated composition, IN-M1 CFS or IN-M2 CFS. Cells were removed by any method known to those of skill in the art, such as by filtering or centrifugation.
Alternate 3

A secondary fermentation culture (a mixed culture) was made from the above seed culture of IN-M1 or IN-M2 to produce a stable concentrated culture (mixed microbial culture) comprising approx. 1 billion microorganisms per liter ($1\times10^6$ cells/mL). A typical 1000 liter secondary fermentation batch, was inoculated with 50 litres of the In-M1 or In-M2 seed culture and the secondary fermentation media contained 15-30 g/l dextrose, 2-8 g/l potato extract, 3.75 liters wheat bran, (0.02-0.05% by volume), 3.75 liters kelp, (0.02-0.05% by volume), 3.75 liters bentonite clay, (0.02-0.05% by volume), 1.25 liters fish emulsion (a commercially available organic soil amendment, from Nutrivert, Dunham, Quebec non-pasteurized, 1.25 liters soy flour, (0.005-0.03% by volume), 675 mg commercially available sea salt, and enough non-chlorinated warm water to make 1000 L.

The pH dropped to about 3.7 by Day 5 after inoculation, and the culture was grown and stirred lightly once per day and pH was monitored. The culture was incubated for 3-10 weeks at 26-33° C. The pH of the final product was adjusted to pH 5 and pH 7 depending on the intended use of the protectant. The composition was bottled and stored under anoxic conditions in airtight containers out of sunlight at room temperature. This resulting composition may be referred to as a concentrated composition, with cells at $1\times10^6$ cells/mL. A cell-free supernatant composition was made by removing the cells from the concentrated composition, IN-M1 CFS or IN-M2 CFS. Cells were removed by any method known to those of skill in the art, such as by filtering or centrifugation.

Example 2—Preparation of a Cell-Free Supernatant

Cell-free supernatant ("CFS") composition was obtained by centrifuging the microbial culture prepared using the methods as described above for at least 10 minutes at a centrifugal force of 14,171×g. The CFS composition was then checked by absorbance (600 nm) to determine whether any microbes were still present and the liquid portion is removed via decanting or pipetting. The supernatant was then filter sterilized with a 0.22 μM micron filter (MCE membrane). The CFS can be filter sterilized using filters or other methods known to those of skill in the art.

Example 3—Use of the Compositions and Methods to Inhibit Fungal Pathogens at Different Dilutions Tournas et al. (2005) (*Crit. Rev. Microbiol.* 31, 33-44) reported that bacterial spoilage of vegetables are most commonly caused by *Erwinia carotovora, Pseudomonas* spp., *Xanthomonas campestris.* The fungi causing the largest impact on the spoilage of fresh vegetables include various species of the genera *Colletotrichum, Fusarium, Phytophthora,* and *Pythium* among many others. In 1980, Kennedy and Alcorn found that over two decades the most significant microorganism causing crop loss, in decreasing order, were *Xanthomonas vesicatoria, E. carotovora, Agrobacterium tumefaciens, Corynebacterium sepedonicum, X. malvacearum, E. amylovora, Pseudomonas glycinea* and *P. syringae* (Kennedy and Alcorn (1980) *Plant Disease* 64, 674-676). At that time the greatest monetary loss was approximately $54,500,000 caused by *P. glycinea* on soybean in Iowa. *Xanthomonas* spp can attack at least 350 different plant diseases. Bacterial blight caused by *Xanthomonas oryzae* pv. *oryzae* is a major disease of rice in tropical Asia and all varieties are highly susceptible (Strange and Scott (2005) *Annu. Rev. Phytopathol.* 43, 83-116).

One of the earliest-described potato diseases, common scab (CS), remains a serious concern for potato growers. There is currently no adequate control for CS, which decreases potato quality and marketability because of scabby or wart-like raised or pitted lesions on the potato tuber skin (Hill and Lazarovits (2005) *Can. J. Plant Pathol.* 27, 46-52; Wilson, C. R. A summary of common scab disease of potato research in Australia. In "Proceedings of the International Potato Scab Symposium" 2004 eds. Naito, S., Kondo, N., Akino, S., Ogoshi, A. and Tanaka, F. pp. 198-214. Sapporo, Japan: Hokkaido University).

*Colletotrichum* spp cause anthracnose in many tropical and subtropical crops. The wide host range of some strains presents a considerable threat to crops. *Phytophthora* spp (meaning plant destroyer) are highly destructive with *P. infestans* costing annually on a global basis in excess of $5 billion in terms of losses of the potato crop and control measures. *Pythium* is another genus that can cause serious disease problems. *P. aphanidermatum* is a major problem in vegetable and ornamental greenhouse production in Ontario and across the world.

The vascular wilt fungi *Verticillium dahliae* and *V. alboatrum* infect over 200 plant species, causing billions of dollars in annual crop losses. The pathogens cause characteristic wilt symptoms that result from colonization and proliferation of the pathogens in the xylem vessels. Infected plants often die or fail to yield a crop. (Klosterman, et al. (2011) *PLoS Pathogen* 7, e1002137).

The two compositions of cell-free supernatant ("CFS"), referred to as "IN-M1 CFS" and "IN-M2 CFS," were tested at the following dilutions: 1/10, 1/20 and 1/40 at the final dilution of the composition in Potato Dextrose Agar (PDA), "PDA plates". The compositions were also tested at pH 7 and pH 5. A preliminary test was done to determine the necessity of filter sterilizing the product before use in the tests. Non-sterilized product was added to PDA plates and incubated at 25° C. for 3 days. Biological growth was observed on every plate and it was determined that the cell-free supernatant composition could be filter-sterilized before use in the toxicity assay. The filter-sterilized cell-free supernatant composition was added directly to the PDA media after the PDA media was first autoclaved and cooled to approximately 45° C. The PDA media was then poured in pre-sterilized plastic petri plates with a diameter of 85 mm.

The following five pathogenic fungi were used in the test: *Pythium ultimum* (representative of the most problematic pathogen in substrate and soil), *Fusarium oxysporum* (pathogen of numerous crop and ornamental plants), *Phytophthora capsici* (causes blight and fruit rot of peppers and other commercial crops), *Colletotrichum coccodes* (tomato and potato pathogen) and *Verticillium dahliae* (causes disease in 300 plant species and most high value crops). The following four pathogenic bacteria were used: *Streptomyces scabies* (causes common scab of potato), *Erwinia carotovora* (causes soft rot of most vegetable crops), *Pseudomonas syringae* (causes lesions on leaves of numerous crops) and *Xanthomonas* (causes spots and blights of leaves, stems and fruit of many crops).

The PDA media plates containing the various dilutions of cell-free supernatant composition were inoculated in triplicate with each of the five fungi by placing a size 2 fungal plug in the center of the plate. The plates were then stored in a 25° C. incubator. The PDA media plates containing the various dilutions of cell-free supernatant composition were inoculated in triplicate with each of the four bacteria by taking a 1 μL loop of stock culture and streaking it onto the plates. The plates were then stored in a 25° C. incubator and left to grow for 4 days. PDA media plates that did not receive any cell-free supernatant composition were used as the control plates.

Inhibition of the fungi was determined by measuring the diameter of growth on each plate and comparing it to control plates. Measurements were taken at day 4, 6 and 8 for *F. oxysporum* and *C. coccodes*, day 1, 2 and 3 for *P. ultimum* and *P. capsici* and day 7 and 12 for *V. dahliae*. Measurement dates were determined based on the speed at which each fungus grew. Inhibition of the bacteria was determined based on the amount of growth relative to the control plates and was checked at day 4 and 8. The dilutions that were used in for this study were determined by preliminary analysis of a wide spectrum of dilutions using a number of selected bacteria and fungi.

A summary of the results is illustrated in Table 2 below.

TABLE 2*

| | % Inhibition | | Days Growth | | % Regrowth Treated Samples (mm) | | | | | |
|---|---|---|---|---|---|---|---|---|---|---|
| Batch Fungi | A | B | A | B | A | B | A | B | A | B |
| | | | | | Day 1 | | Day 2 | | Day 3 | |
| Pythium ultimum | 10.5 | 30.5 | | | 10 | 15 | 42 | 30 | 75 | 60 |
| | 29 | 50.5 | | | 12 | 10 | 30 | 20 | 60 | 40 |
| | | 14.5 | | | 20 | 12 | 50 | 40 | 84 | 75 |
| Batch Fungi | A | B | A | B | A | B | A | B | A | B |
| | | | | | Day 4 | | Day 6 | | Day 8 | |
| Fusarium oxysporum | 33.8 | 45.2 | | | 25 | 18 | 40 | 31 | 45 | 38 |
| | 13.7 | 28.7 | | | 35 | 30 | 50 | 45 | 65 | 64 |
| | 6.8 | 26.9 | | | 40 | 32 | 60 | 43 | 69 | 52 |
| | 46 | 33 | | | 16 | 12 | 24 | 30 | 31 | 41 |
| | 14.5 | 23 | | | 36 | 21 | 40 | 34 | 48 | 42 |
| | 16.4 | 6.7 | | | 29 | 25 | 42 | 40 | 54 | 48 |
| Batch Fungi | A | B | A | B | A | B | A | B | A | B |
| | | | | | Day 1 | | Day 2 | | Day 3 | |
| Phytophthora capsici | 59.6 | 100 | | | 10 | 0 | 15 | 0 | 20 | 0 |
| | 10.7 | 8.9 | | | 20 | 18 | 35 | 33 | 50 | 52 |

TABLE 2*-continued

| | % Inhibition | | Days Growth | | % Regrowth Treated Samples (mm) | | | | | |
|---|---|---|---|---|---|---|---|---|---|---|
| | 100 | 100 | | | 0 | 0 | 0 | 0 | 0 | 0 |
| | 27.8 | 65.2 | | | 15 | 9 | 23 | 13 | 38 | 18 |
| Batch Fungi | A | B | A | B | A | B | A | B | A | B |
| | | | | | Day 4 | | Day 6 | | Day 8 | |
| Colletotrichum coccodes | 35.7 | 84 | | | 0 | 0 | 20 | 0 | 38 | 18 |
| | | 46.4 | | | | 0 | | 16 | | 30 |
| | | 26.7 | | | | 18 | | 29 | | 42 |
| | 100 | 100 | | | 0 | 0 | 0 | 0 | 0 | 0 |
| | 32.8 | 47.7 | | | 12 | 0 | 27 | 12 | 28 | 26 |
| | | 22.5 | | | | 11 | | 25 | | 42 |
| Batch Fungi | A | B | A | B | A | B | A | B | A | B |
| | | | | | Day 7 | | Day 12 | | | |
| Verticillium dahlia | 59 | 100 | | | 0 | 0 | 16 | 0 | | |
| | 11.1 | 22.2 | | | 20 | 16 | 35 | 30 | | |
| | | 19.7 | | | | | | 31 | | |
| | 100 | 100 | | | 0 | 0 | 0 | 0 | | |
| | 33.6 | 35.2 | | | 14 | 12.5 | 25 | 26 | | |
| | 14.5 | 21.5 | | | 18 | 30 | 32 | 30 | | |
| Batch Bacteria | A | B | A | B | A | B | A | B | A | B |
| Streptomyces scabies | 100 | 100 | 4 | 4 | | | | | | |
| | 100 | 100 | 4 | 4 | | | | | | |
| Erwinia carotovora | 100 | 100 | 4 | 4 | | | | | | |
| | 100 | 100 | 4 | 4 | | | | | | |
| Pseudomonas syringae | 80 | 80 | 4 | 4 | | | | | | |
| | 100 | 100 | 4 | 4 | | | | | | |
| Xanthomonas | 50 | 100 | 4 | 4 | | | | | | |
| | 60 | 60 | 4 | 4 | | | | | | |

* "Batch A" refers to IN-M1 CFS and "Batch B" refers to IN-M2 CFS.

*Streptomyces scabies*

At a pH of 7 and a dilution of 1/10 IN-M1 CFS inhibited all growth of *S. scabies*. At a pH of 7 and a dilution of 1/10 and 1/20, IN-M2 CFS inhibited all growth of *S. scabies*. At a pH of 5, IN-M1 CFS and IN-M2 CFS both inhibited all growth of *S. scabies* at all three dilutions.

*Erwinia carotovora*

At a pH of 7 and a dilution of 1/10, IN-M1 CFS and IN-M2 CFS inhibited all growth of *E. carotovora*. At a pH of 5, IN-M1 CFS and IN-M2 CFS inhibited all growth of *E. carotovora* at all three dilutions.

*Xanthomonas*

At a pH of 7 and a dilution of 1/10, IN-M1 CFS inhibited the growth of *Xanthomonas* but did not completely prevent it from growing. At a pH of 7 and a dilution of 1/10, IN-M2 CFS inhibited all growth of *Xanthomonas*. At a pH of 5 and a concentration of 1/10, IN-M1 CFS and IN-M2 CFS inhibited all growth of *Xanthomonas*. At pH 5 and dilution of 1/20 and 1/40, IN-M1 CFS and IN-M2 CFS inhibited the growth of *Xanthomonas* but did not completely prevent growth.

*Pseudomonas syringae*

At pH 7 and a dilution of 1/10 and 1/20, IN-M1 CFS and IN-M2 CFS inhibited the growth of *P. syringae*. At pH 5 IN-M1 CFS and IN-M2 CFS inhibited all growth of *P. syringae* at all three dilutions.

*Phytophthora capsici*

Figure 1B:
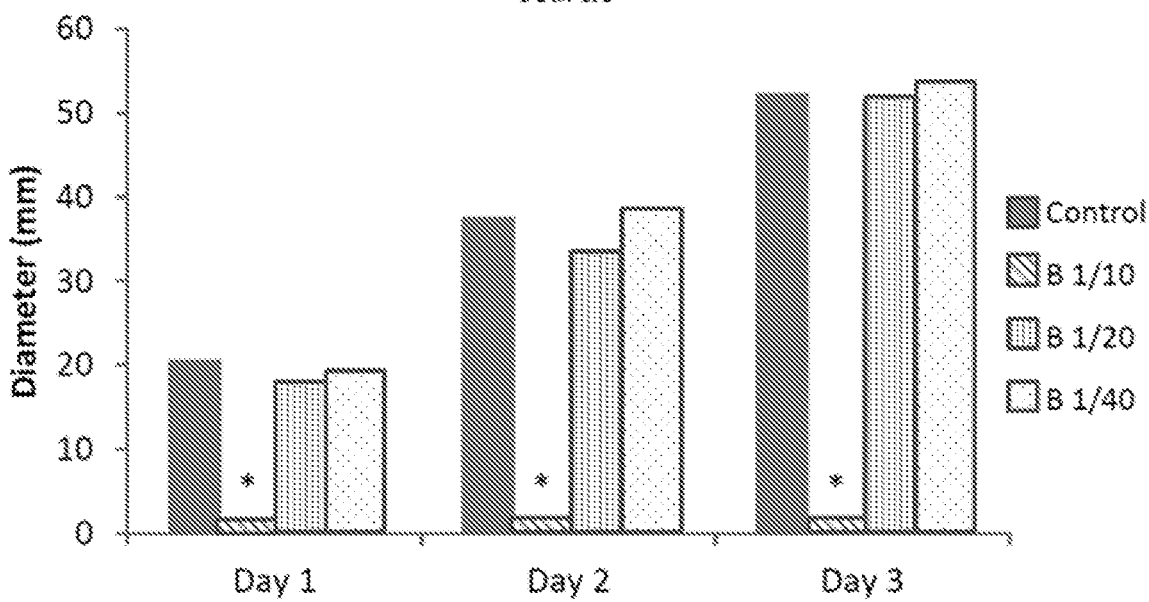

At pH 7 IN-M1 CFS and IN-M2 CFS inhibited the growth of *P. capsici* at a dilution of 1/10 and 1/20. Relative to the control at pH 7, IN-M1 CFS reduced the growth of *P. capsici* by 59.6% at 1/10 and 10.7% at 1/20 (FIG. 1A). Relative to the control at pH 7, IN-M2 CFS reduced the growth of *P. capsici* by 100% at 1/10 and 8.9% at 1/20 (FIG. 1B).

Figure 2A:
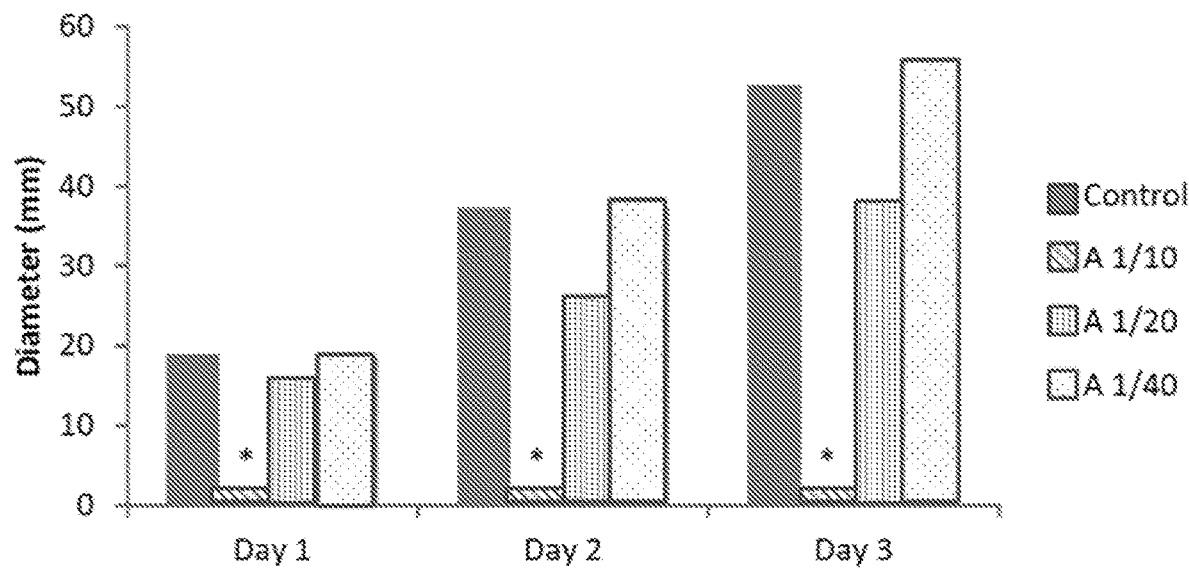
FIGS. 2A and 2B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (2B) on the growth of *P. capsici* at pH 5.
Figure 2B:
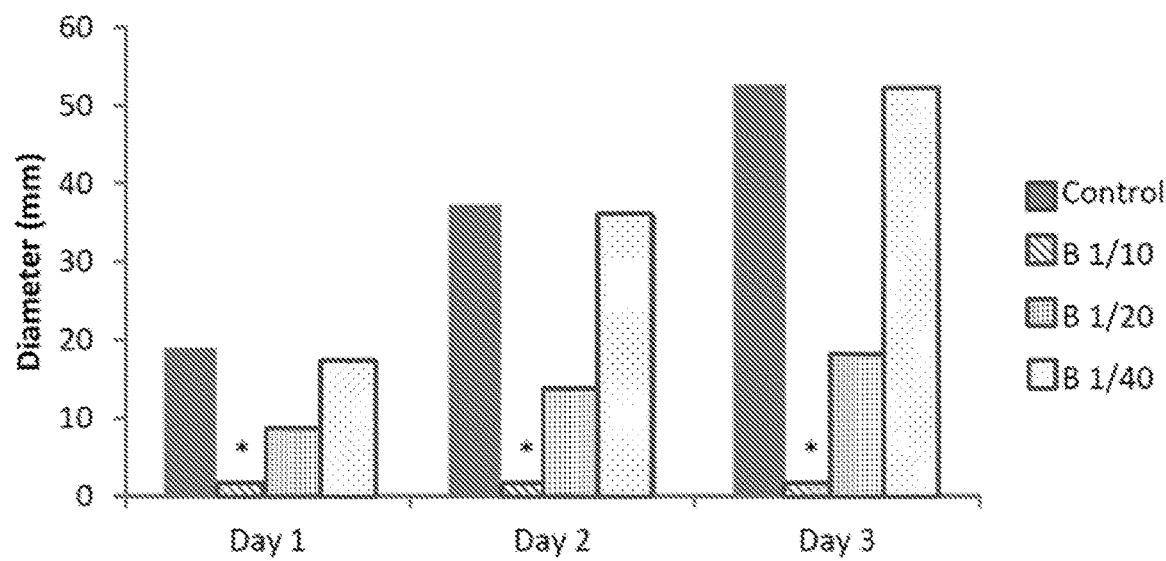

At pH 5 IN-M1 CFS and IN-M2 CFS inhibited the growth of *P. capsici* at a dilution of 1/10 and 1/20. Relative to the control at pH 5, IN-M1 CFS reduced the growth of *P. capsici* by 100% at 1/10 and 27.8% at 1/20 (FIG. 2A). Relative to the control at pH 5, IN-M2 CFS reduced the growth of *P. capsici* by 100% at 1/10 and 65.2% at 1/20 (FIG. 2B).

*Pythium ultimum*

Figure 3A:
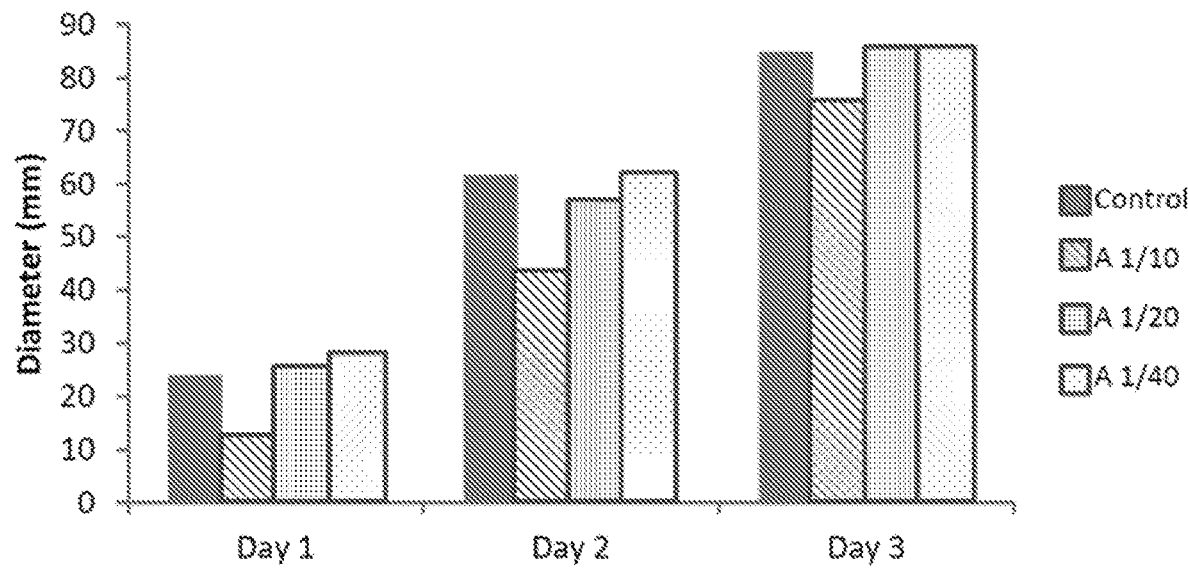
FIGS. 3A and 3B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (3B) on the growth of *P. ultimum* at pH 7.
Figure 3B:
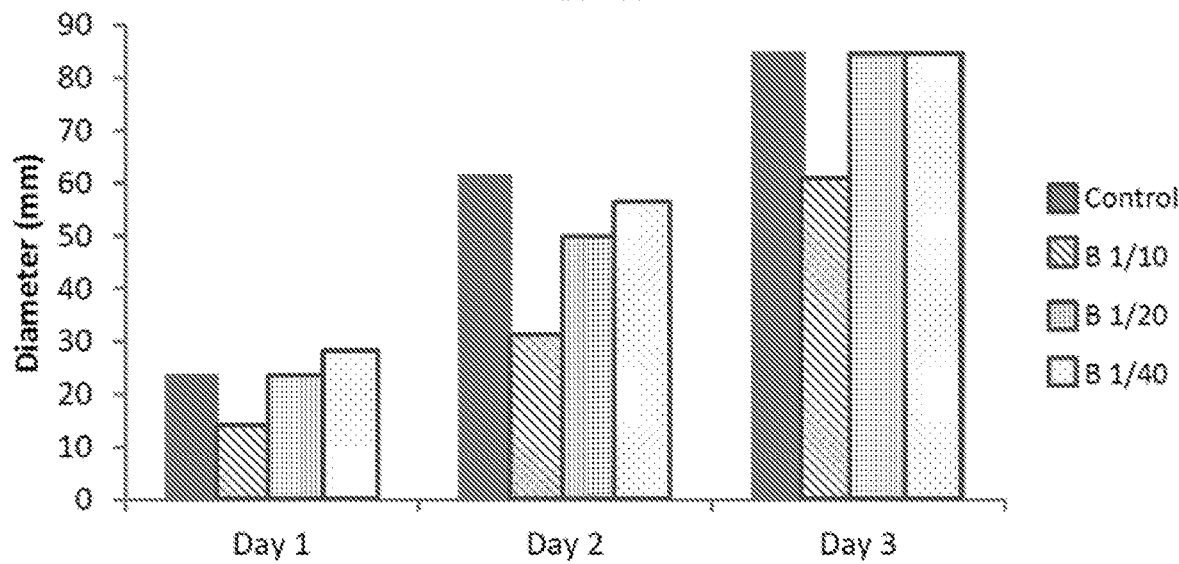

At pH 7, IN-M1 CFS and IN-M2 CFS had minimal effects on the growth of *P. ultimum*. At a dilution of 1/10, IN-M1 CFS only reduced the growth of *P. ultimum* by 10.5% (FIG. 3A). IN-M2 CFS had more of an effect than IN-M1 CFS and reduced the growth of *P. ultimum* by 30.5% at the 1/10 dilution (FIG. 3B). At pH 5 IN-M1 CFS and IN-M2 CFS had slightly more effect on the growth *P. ultimum* than at a pH of 7. At pH 5 and a dilution of 1/10, IN-M1 CFS reduced the growth of *P. ultimum* by 29% (FIG. 1A). At pH 5 IN-M2 CFS reduced the growth of *P. ultimum* by 50.5% at 1/10 and 14.5% at 1/20 (FIG. 1B).

*Fusarium oxysporum*

At pH 7, IN-M1 CFS and IN-M2 CFS inhibited the growth of *F. oxysporum* at all three dilutions. At pH 7, IN-M1 CFS reduced the growth of *F. oxysporum* by 33.8% at 1/10, 13.7% at 1/20 and 6.8% at 1/40 (FIG. 2A). At pH 7, IN-M2 CFS reduced the growth of E *oxysporum* by 45.2% at 1/10, 28.7% at 1/20 and 26.9% at 1/40 (FIG. 2B).

At pH 5, IN-M1 CFS and IN-M2 CFS inhibited the growth of *F. oxysporum* at all three dilutions. At pH 5, IN-M1 CFS reduced the growth of *F. oxysporum* by 46% at 1/10, 17.5% at 1/20 and 16.4% at 1/40 (FIG. 3A). At pH 5, IN-M2 CFS reduced the growth of *F. oxysporum* by 33% at 1/10, 23.5% at 1/20 and 6.7% at 1/40 (FIG. 3B).

*Colletotrichum coccodes*

Figure 4A:
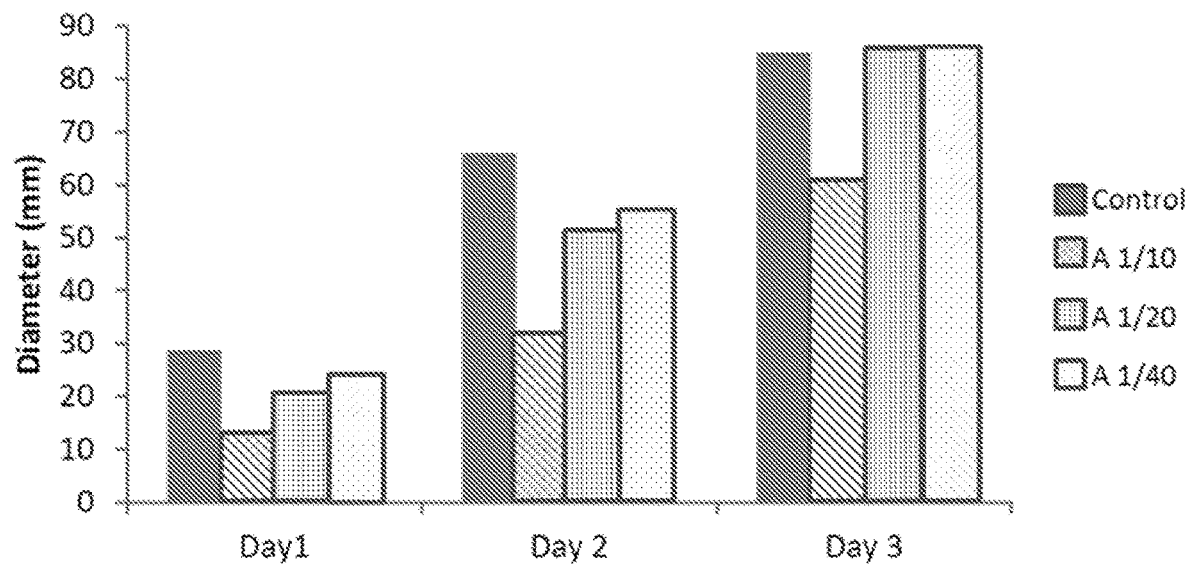
FIGS. 4A and 4B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (4B) on the growth of *P. ultimum* at pH 5.
Figure 4B:
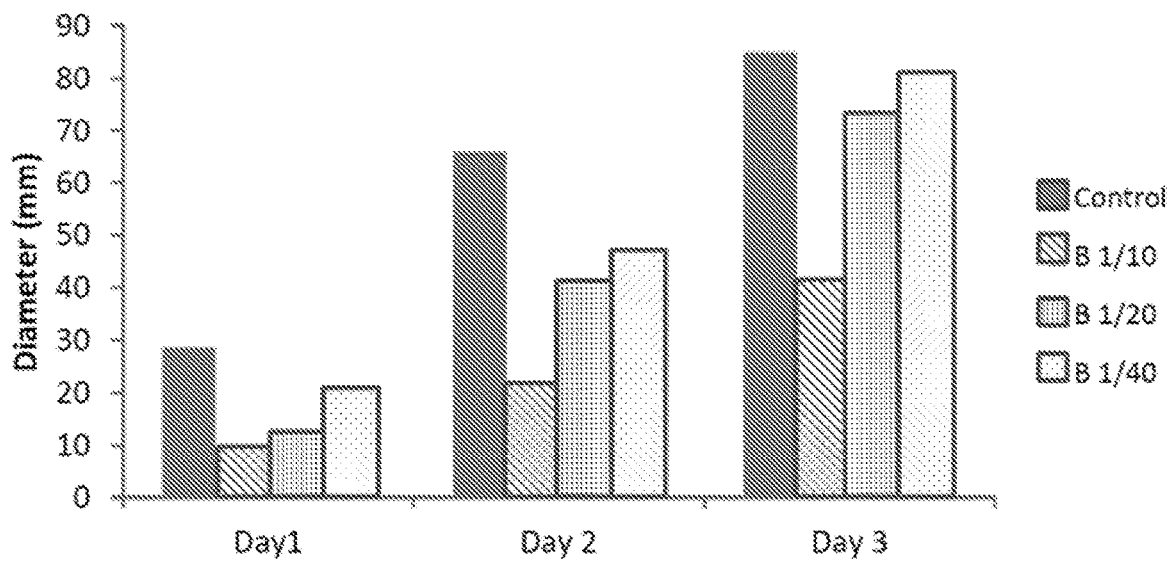
Figure 5A:
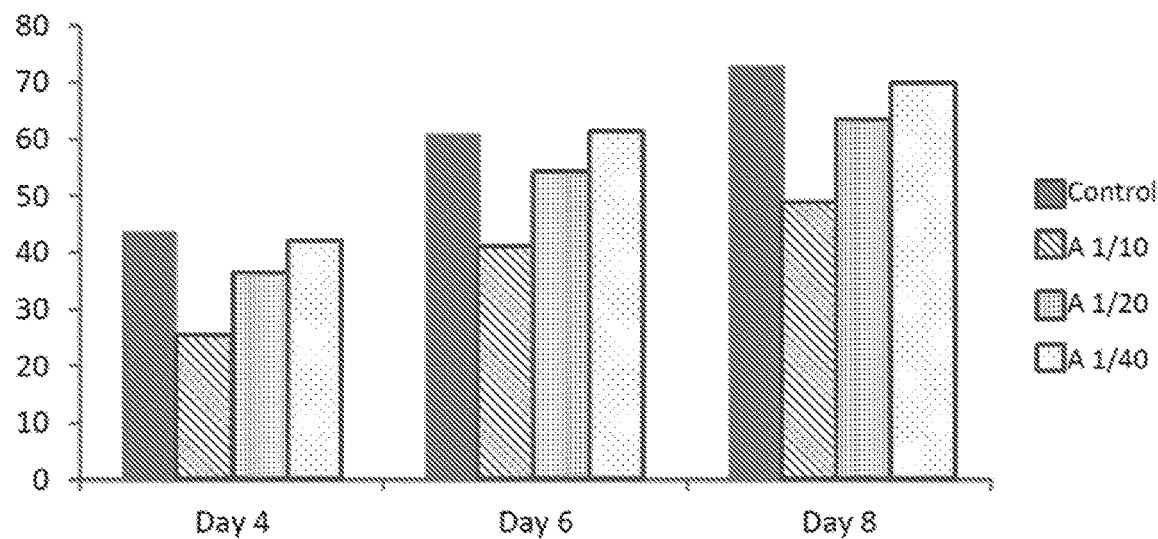
FIGS. 5A and 5B show representative data pertaining to the effect of various dilutions of a cell-free supernatant derived from a microbial fermentation culture of IN-M1 deposited Jan. 11, 2012 with ATCC, PTA-12383 (Inocucor A) (5A) and a cell-free supernatant derived from a microbial fermentation culture of IN-M2 deposited Sep. 4, 2014 with ATCC, PTA-121556, (Inocucor B) (5B) on the growth of *F. oxysporum* at pH 7.
Figure 5B:
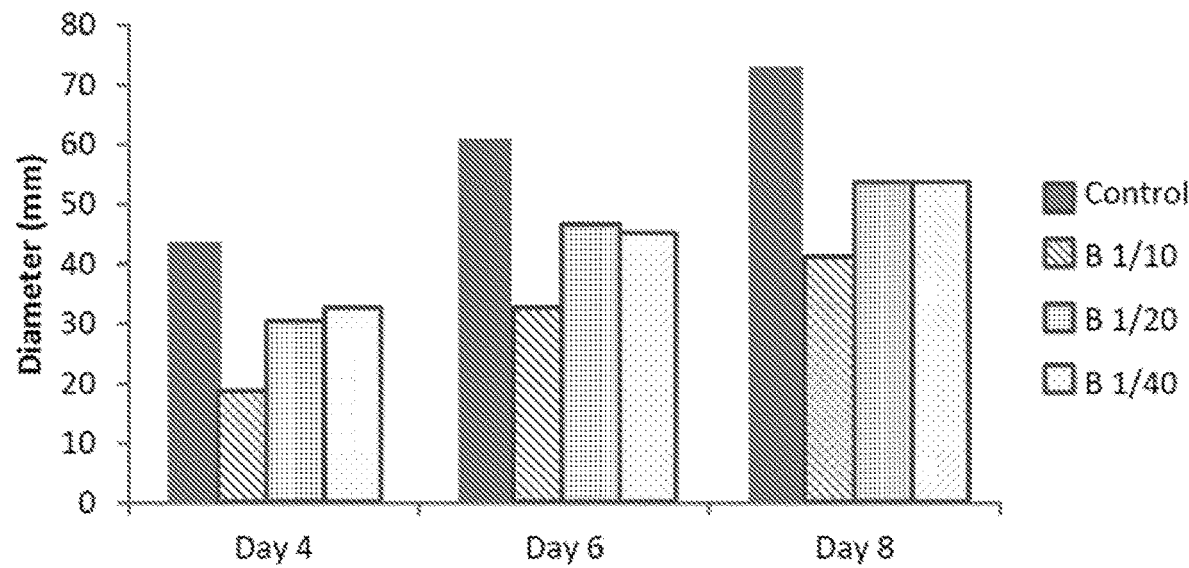

At pH 7, IN-M1 CFS inhibited the growth of *C. coccodes* at a dilution of 1/10. At pH 7, IN-M2 inhibited the growth of *C. coccodes* at all three dilutions. Relative to the control at pH 7, IN-M1 CFS reduced the growth of *C. coccodes* by 35.7% at 1/10 (FIG. 4A). Relative to the control at pH 7, IN-M2 CFS reduced the growth of *C. coccodes* by 84% at 1/10, 46.4% at 1/20 and 26.7% at 1/40 (FIG. 4B). At pH 5, IN-M1 CFS inhibited the growth of *C. coccodes* at 1/10 and 1/20. The plates for IN-M2 CFS at pH 5 did not grow as well as the plates for IN-M1. Based on the plates that did grow, IN-M2 CFS inhibited the growth of *C. coccodes* at all three dilutions. Relative to the control at pH 5, IN-M1 CFS reduced the growth of *C. coccodes* by 100% at 1/10 and 32.8% at 1/20 (FIG. 5A). Relative to the control at pH 5, IN-M2 CFS reduced the growth of *C. coccodes* by 100% at 1/10, 47.7% at 1/20 and 22.5% at 1/40 (FIG. 5B).

*Verticillium dahliae*

Figure 6A:
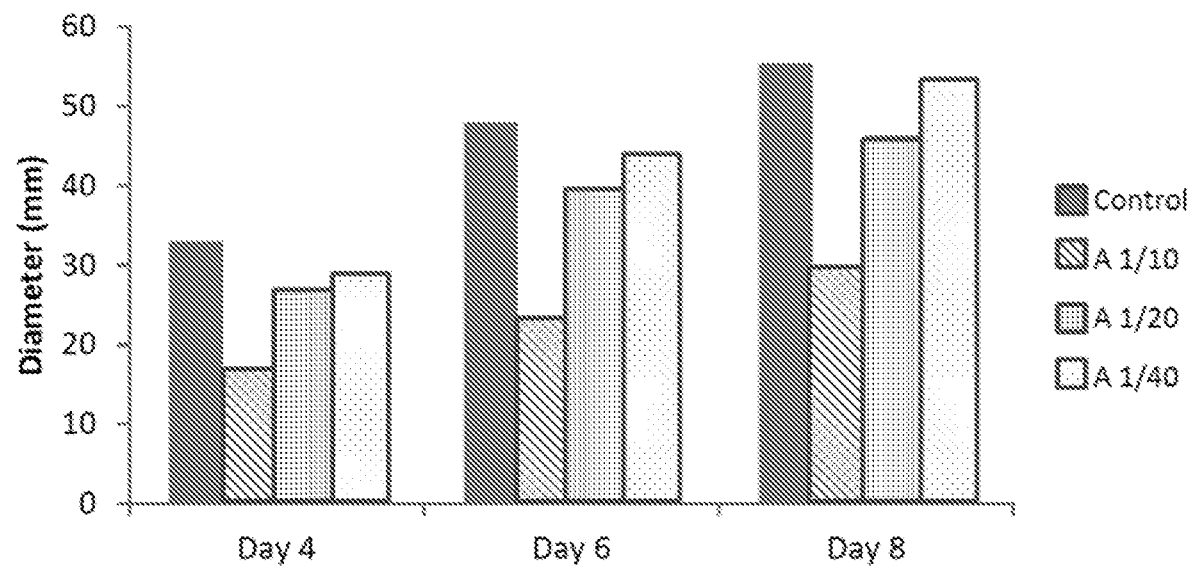
FIGS. 6A and 6B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (6B) on the growth of *F. oxysporum* at pH 5.
Figure 6B:
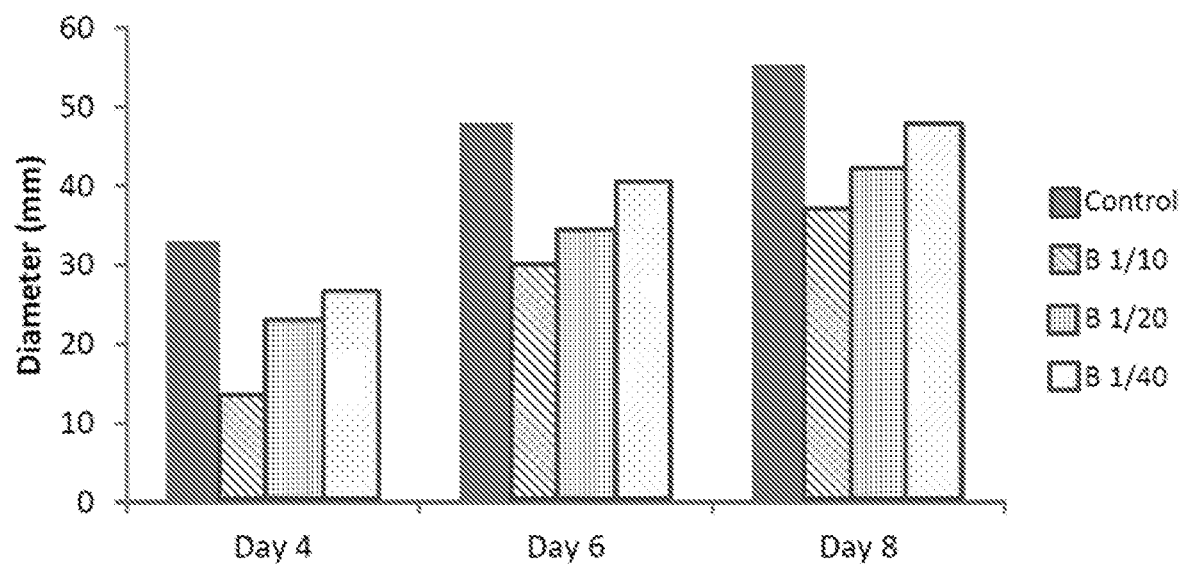

At pH 7, IN-M1 CFS inhibited the growth of *V. dahliae* at a dilution of 1/10 and 1/20. At pH 7, IN-M2 CFS inhibited the growth of *V. dahliae* at all three dilutions. Relative to the control at pH 7, IN-M1 CFS reduced the growth of *V. dahliae* by 59% at 1/10 and 11.1% at 1/20 (FIG. 6A). Relative to the control at pH 7, IN-M2 CFS reduced the growth of *V. dahliae* by 100% at 1/10, 22.2% at 1/20 and 19.7% at 1/40 (FIG. 6B).

Figure 7A:
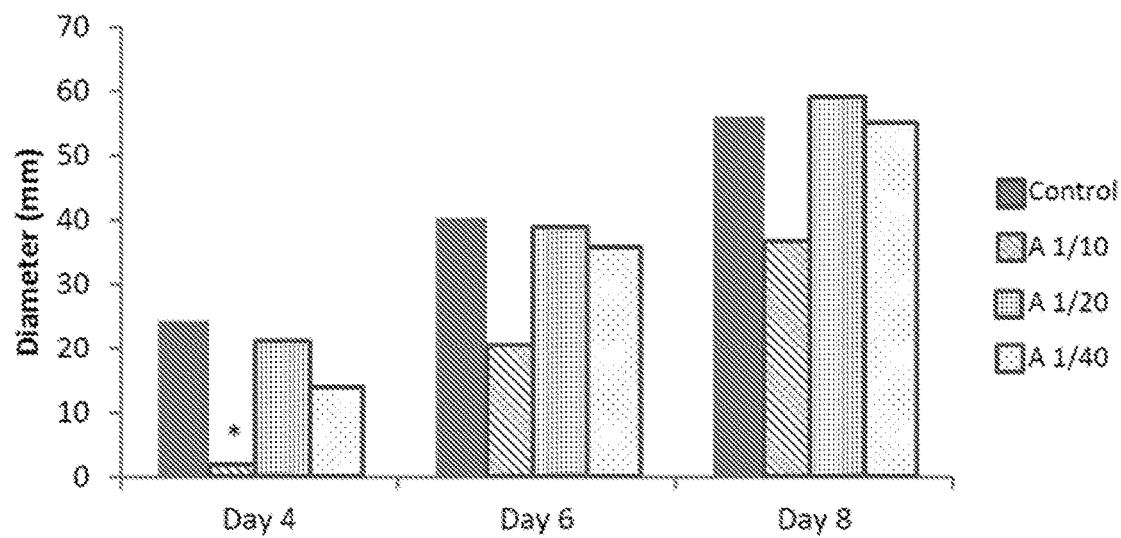
FIGS. 7A and 7B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (7B) on the growth of *C. coccodes* at pH 7.
Figure 7B:
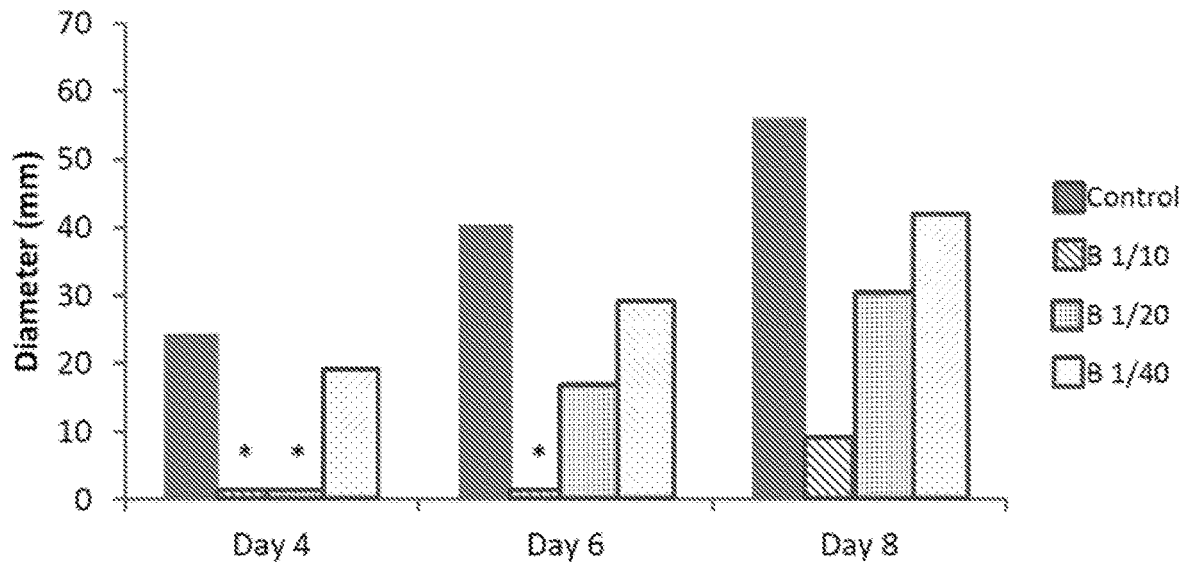
Figure 8A:
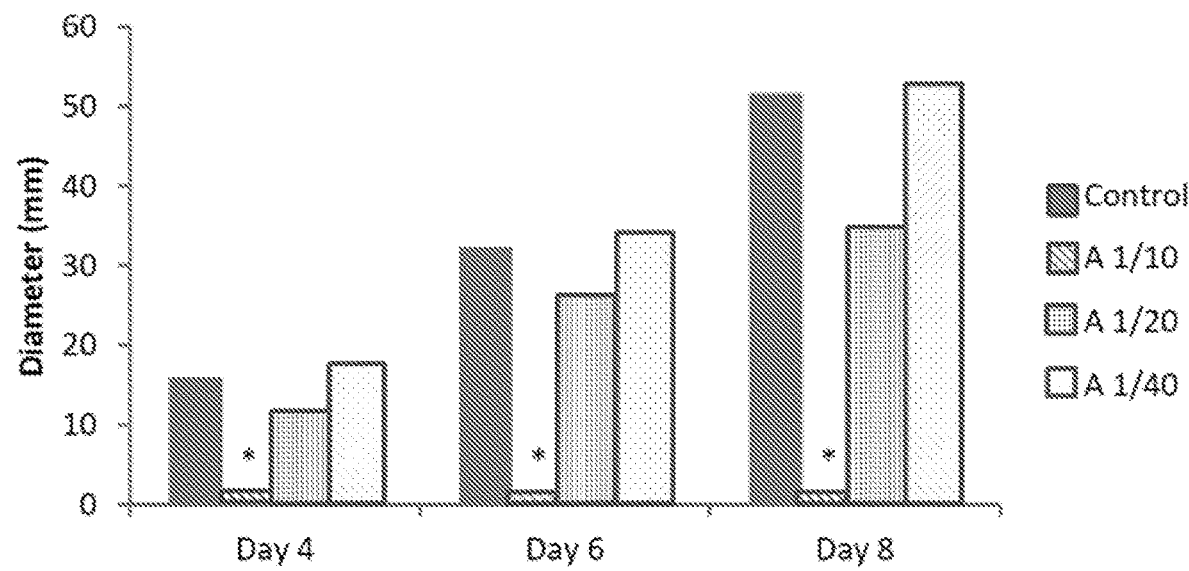
FIGS. 8A and 8B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (8B) on the growth of *C. coccodes* at pH 5.
Figure 8B:
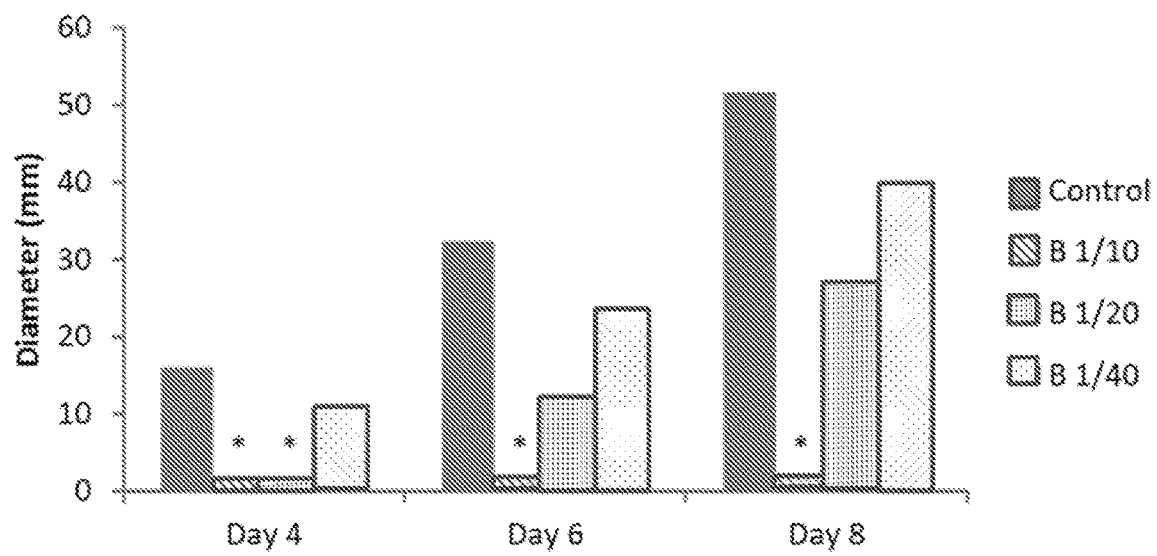
Figure 9A:
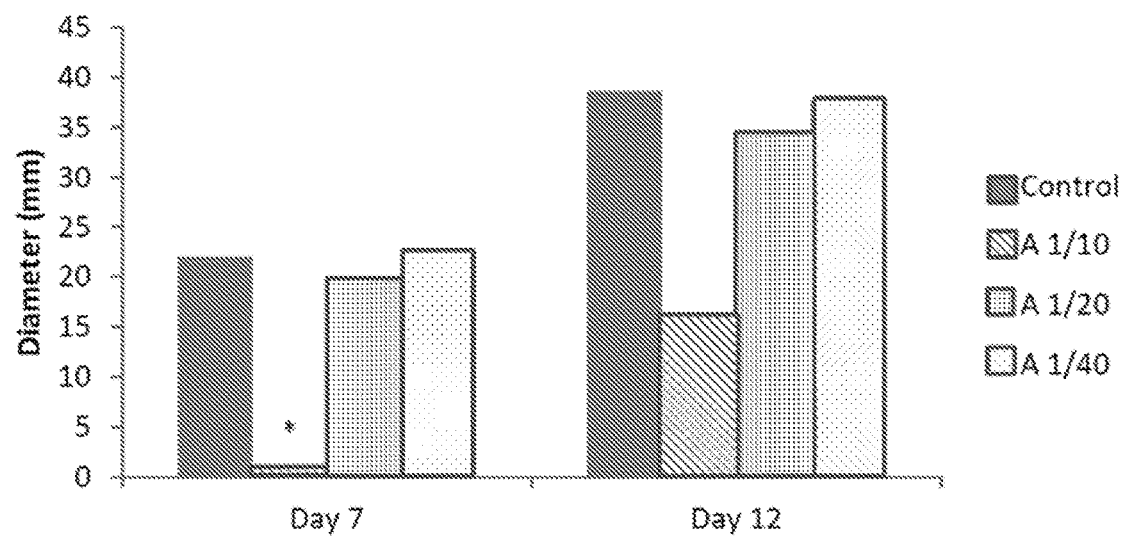
FIGS. 9A and 9B show representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (9B) on the growth of *V. dahliae* at pH 7.
Figure 9B:
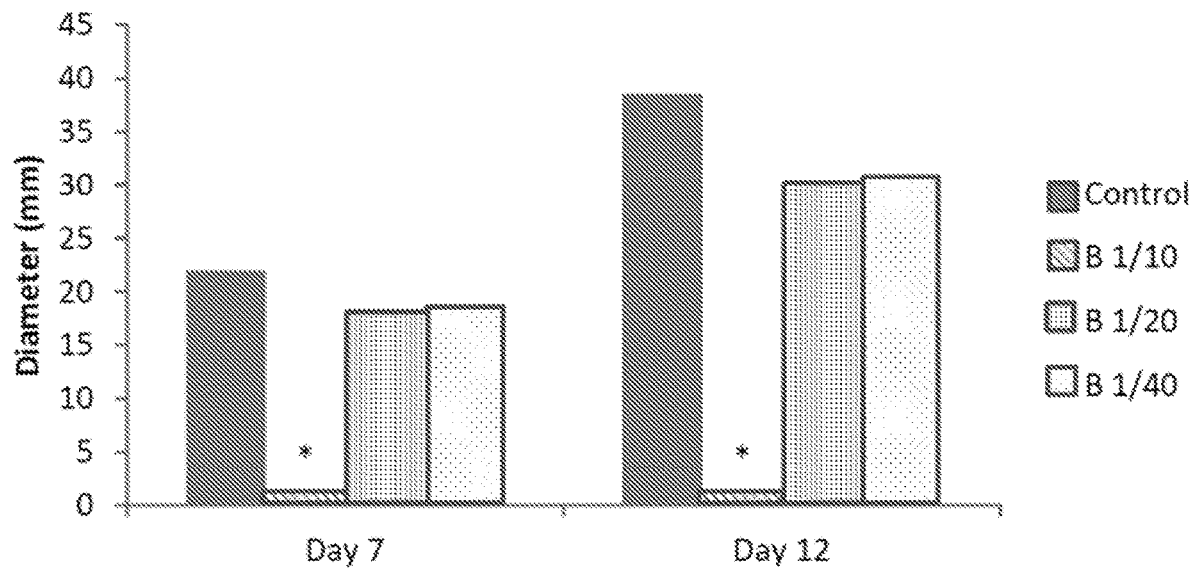
Figure 10A:
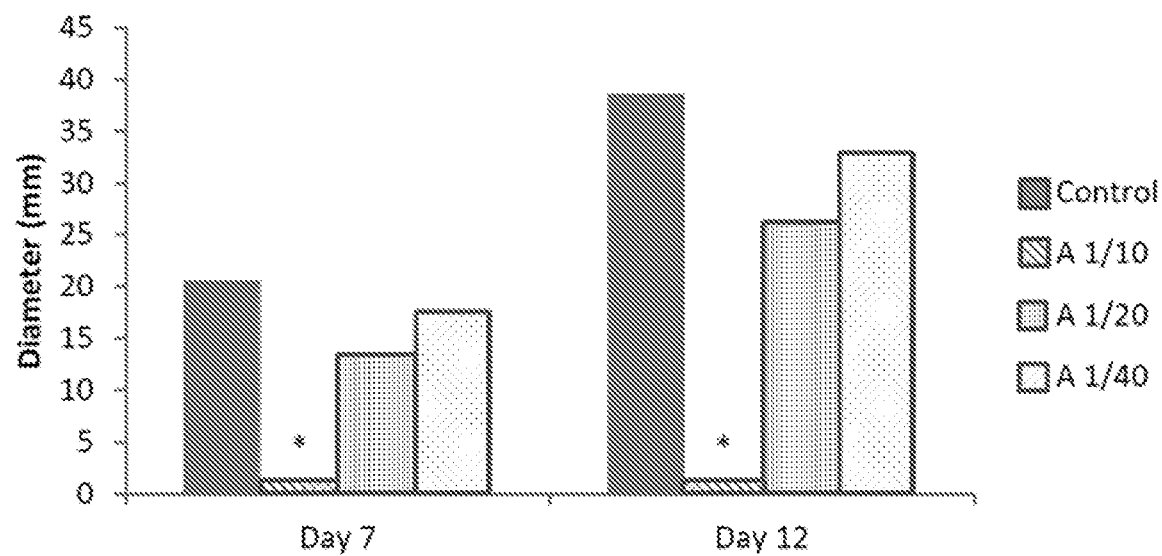
FIGS. 10A and 10B show shows representative data pertaining to the effect of various dilutions of a cell-free supernatant derived from a microbial fermentation culture of IN-M1 deposited Jan. 11, 2012 with ATCC, PTA-12383, (Inocucor A) (1A) and a cell-free supernatant derived from a microbial fermentation culture of IN-M2 deposited Sep. 4, 2014 with ATCC, PTA-121556, (Inocucor B) (10B) on the growth of *V. dahliae* at pH 5.
Figure 10B:
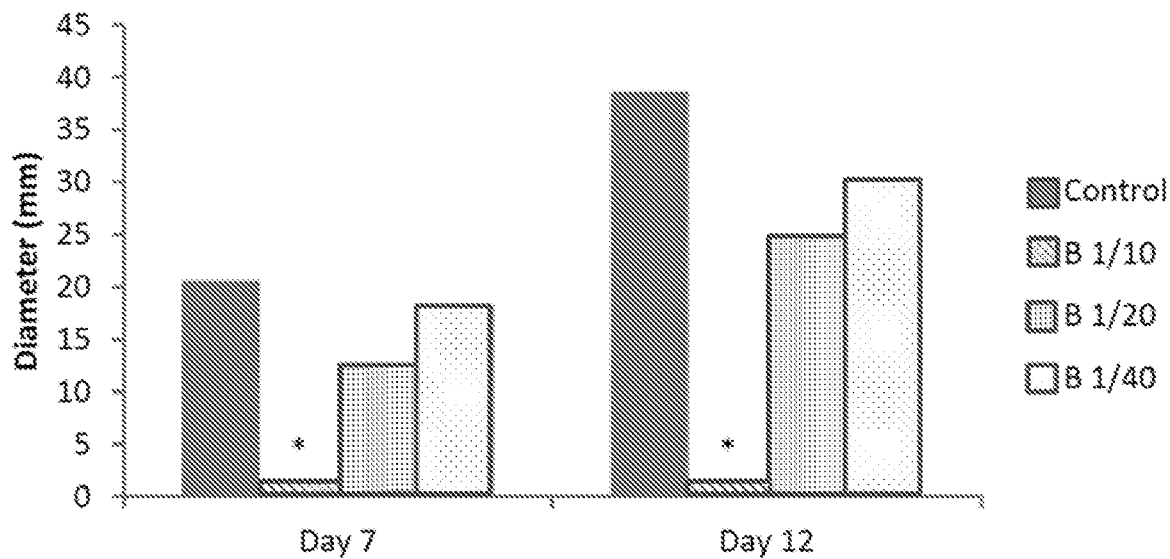

At pH 5, IN-M1 CFS and IN-M2 CFS inhibited the growth of *V. dahliae* at all three dilutions. Relative to the control at pH 5, IN-M1 CFS reduced the growth of *V. dahliae* by 100% at 1/10, 33.6% at 1/20 and 14/5% at 1/40 (FIG. 7A). Relative to the control at pH 5, IN-M2 CFS reduced the growth of *V. dahliae* by 100% at 1/10, 35.2% at 1/20 and 21.5% at 1/40 (FIG. 7B).

In summary, at a pH of 7 and a dilution of 1/10, both IN-M1 CFS and IN-M2 CFS completely inhibited the growth of *S. scabies, E. carotovora, Xanthomonas* and *P. syringae*. At a pH of 5, IN-M1 CFS and IN-M2 CFS completely inhibited the growth of *S. scabies, E. carotovora*, and *P. syringae* at all three dilutions. At pH 5 *Xanthomonas* was inhibited but some growth was still observed on each of the plates at dilutions of 1/20 and 1/40. Without wishing to be bound by theory, the difference in inhibition may be due to the action of volatile fatty acids ("VFAs"), i.e., organic compounds that are low-molecular weight carboxylic acids with aliphatic tails of 6 carbon atoms or less which include, but are not limited to, acetic acid, butyric acid, lactic acid, propionic acid, and pyruvic acid.

At pH of 7 or 5 and a dilution of 1/10 all five fungal pathogens were either partially or completely inhibited in their growth on IN-M1 CFS and IN-M2 CFS treated plates. At pH 5 and a dilution of 1/10 *V. dahliae, C. coccodes, P. capsici* were completely inhibited by both products. IN-M1 CFS and IN-M2 CFS were most effective on *F. oxysporum* and *V. dahliae* and least effective on *P. ultimum*. The compositions disclosed herein offer significant bioprotectant control for a number of diverse high value crops.

No pathogens were prevented from growing at a dilution of 1/20, but all but *P. ultimum* were still inhibited at this dilution at both pH 7 and 5. The 1/10 dilution of both cell-free supernatant compositions was the most effective at inhibiting and/or eliminating the pathogens tested. Both cell-free supernatant compositions were more effective at inhibiting both bacterial and fungal pathogens at a pH of 5. In general, IN-M2 CFS was more effective at inhibiting the fungal pathogens than IN-M1 CFS. Without wishing to be bound by theory, these data may provide guidance towards the development of more bioactive formulations. For example, compositions of the present disclosure may comprise buffering agents to maintain the pH in an effective range.

Example 4 Reducing Damage by Powdery Mildew

Powdery mildew is a fungal disease that affects a wide range of plants. Powdery mildew diseases are caused by many different species of fungi in the order Erysiphales, with *Podosphaera xanthii* (a.k.a. *Sphaerotheca fuliginea*) being the most commonly reported cause. *Erysiphe cichoracearum* was formerly reported to be the primary causal organism throughout most of the world. Powdery mildew is one of the easier plant diseases to identify, as its symptoms are quite distinctive. Infected plants display white powdery spots on the leaves and stems. The lower leaves are the most affected, but the mildew can appear on any above-ground part of the plant. As the disease progresses, the spots get larger and denser as large numbers of asexual spores are formed, and the mildew may spread up and down the length of the plant.

Powdery mildew grows well in environments with high humidity and moderate temperatures. The resulting disease can significantly reduce crop yields. Greenhouses provide an ideal moist, temperate environment for the spread of the disease.

Tomato plants were infected with powdery mildew and once the powdery mildew was visible, a foliar spray of a cell-free supernatant derived from a microbial culture of IN-M1 was applied to the leaves, stalks and plant parts above the soil. After two weeks, the powdery mildew was not detectable. The treated tomato plants grew better, had more vigor and produced more tomatoes than did the untreated tomato plants that had powdery mildew and were not treated with the foliar spray of a cell-free supernatant derived from a microbial culture of IN-M1.

Example 5 Controlling Damage by Charcoal Rot

Collapsing strawberry plants have been associated with the soilborne fungus *Macrophomina phaseolina*. The disease, called charcoal rot, appears to be the most important current concern for the industry due to its steady increase. Each year finds additional new fields infested, and the disease has now been found in many major strawberry producing states. The spread of *Macrophomina* to new fields and counties portends that charcoal rot may be a long term threat to the industry which at present does not have satisfactory plant resistance with which to combat the pathogen.

Symptoms of *Macrophomina* infection in strawberry consist of wilting of foliage, plant stunting, and drying and death of older leaves, with the central youngest leaves often remaining green and alive. Plants can eventually collapse and die. When plant crowns are cut open, internal vascular and cortex tissues are dark to orange brown. Disease is often most severe if the infected plant is subject to stresses such as weather extremes, water stress (shortage of water), poor soil conditions, or heavy fruit loads. In locations where the disease has occurred for more than one season, the patches can be quite large and appear to have spread from the initial problem area.

Strawberry plants were infected with *Macrophomina* and once the charcoal rot was visible, a foliar spray of a cell-free supernatant derived from a microbial culture of IN-M1 was applied to the leaves and plant parts above the soil. After two weeks, the charcoal rot was not detectable and the new leaves that grew in were not infected. The treated strawberry plants grew better, had more vigor and produced more strawberries than did the untreated strawberry plants that had charcoal rot and were not treated with the foliar spray of a cell-free supernatant derived from a microbial culture of IN-M1.

Example 6 Reducing Phythoptera in Transplanted Plants

Strawberry infection by *Phytophthora cactorum* occurs on poorly drained, over-irrigated soils, or during long periods of rain in warm climates. Symptoms of disease are enhanced during periods of high water need, such as after transplants are set, during hot dry weather, or as the fruit load increases. The pathogen has become very important in the last 10-15 years.

The most diagnostic feature of plants with advanced symptoms is a collapse of plants and a deep dark red discoloration of the crown. Stunting of plants or wilting of young leaves are the first symptoms and may appear at any time during the season. Infected plants may remain stunted, or foliage may turn bluish and the entire plant may wilt rapidly until total collapse. Wilting is often accompanied by "draught" symptoms on the leaves such as browning of leaf margins often progressing between the veins and a sharp line between damaged and healthy tissue. Roots attached to the affected crown area are frequently black at the point of attachment and commonly have diagnostic oospores in the root tissue. Root systems are also frequently discolored and have a low level of fibrous (secondary and tertiary) roots.

The disease can appear in plug production facilities introduced on infected tips or through contaminated water sources. Tips fail to root, the roots turn black, and the lower petioles of the leaves turn dark brown to black. Plug plants will die or remain stunted especially once frequent watering stops.

Infection is favored by wet conditions. The primary inoculum sources include oospores in the soil and infected transplants. Disease expression is influenced by time of planting and environmental conditions. Since the fungus requires warm temperatures and prolonged wetness, initial plant collapse can occur in the fall within 1 month after planting with additional plant collapse occurring the following spring as regrowth occurs and especially as fruit develop. The pathogen can move with water flow patterns in the field and in plug production facilities.

Treated strawberry plants that were being transplanted into a field were dipped in transplantation water that was 50% cell-free supernatant derived from a microbial culture of IN-M1. The treated plants were planted in a field where *Phytophthora* was present and the field conditions were flooding or overwatering. The treated strawberry plants grew better, had more vigor and produced more strawberries than did the untreated strawberry plants that were not treated with the transplanting water comprising a cell-free supernatant derived from a microbial culture of IN-M1.

It will be apparent to those skilled in the art that various modifications and variations can be made in the present disclosure without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for protecting a plant from a damage due to a plant pathogen comprising,
   contacting the plant, or a soil or a plant growth media for the plant, with a bioprotectant composition comprising a cell-free supernatant of a microbial culture and diluent water,
   wherein the cell free supernatant is produced by
       inoculating IN-M1, deposited under ATCC Accession No. PTA-12383, or IN-M2, deposited under ATCC Accession No. PTA-121556 into a culture media comprising water, molasses, mineral powder, sea salt, and wheat bran; and
       incubating the inoculated culture media for 3-10 weeks at 30-32 or 35-37 or 32-37 degrees Celsius to obtain a microbial culture; and
       centrifuging the microbial culture to separate microbial culture cells from a supernatant; and
       filter sterilizing the supernatant to obtain the cell-free supernatant of the microbial culture, wherein the cell free supernatant comprises high levels of potassium, nitrogen, calcium, and magnesium, and significant levels of volatile fatty acids;
   wherein the ratio between the cell-free supernatant and the diluent water is between 1:25 and 1:1000; and
   wherein the plant has been infected with the plant pathogen, and
   wherein the plant has reduced pathological damage after the step of contacting with the bioprotectant composition compared to an untreated control plant.

2. The method of claim 1, wherein the bioprotectant composition further comprises an herbicide, a pesticide, a nematocide, a fungicide, a fertilizer, or a nutrient component, or a combination thereof.

3. The method of claim 1, wherein the culture media comprises humic acid, potato starch, or molasses.

4. The method of claim 1, wherein the bioprotectant composition further comprises a wetting agent, a gelling agent, a higher fatty acid, 3-hydroxydecanoic acid, 3-hydroxydodecanoic acid, 3-hydroxytetradecanoic acid, 3-hydroxy-5-cis-dodecenoic acid, a volatile fatty acid, acetic acid, butyric acid, isobutyric acid, propionic acid, or a combination thereof.

5. The method of claim 1, wherein the pH of the bioprotectant composition is from pH 5.0 to 7.0.

6. The method of claim 1, wherein the plant is rice, wheat, corn, tomato, banana, coffee, soybean, potato, a citrus, orange, grapefruit, lemon, lime, cucumber, cauliflower, strawberry, a vegetable plant, an ornamental plant or a tree.

7. The method of claim 1, wherein the step of contacting the plant comprises contacting plant parts, seeds, roots, shoots, tubers, leaves or stalks of the plant with the bioprotectant composition.

8. The method of claim 1, wherein the step of contacting with the bioprotectant composition comprises contacting the soil or the plant growth media for the plant with the bioprotectant composition.

9. The method of claim 1, wherein the plant is grown under hydroponic conditions, aeroponic conditions or combined aeroponic and hydroponic conditions.

10. The method of claim 1, wherein the plant is grown in a greenhouse or in a field.

11. The method of claim 1, wherein the step of contacting comprises contacting seeds of the plant with the bioprotectant composition prior to planting the seeds or prior to storage of the seeds.

12. The method of claim 1, wherein the step of contacting is performed during transplantation of the plant, during the plant's vegetative stage, at the plant's flowering stage, at the plant's reproductive stage, or a combination thereof.

13. The method of claim 1, wherein the plant has been infected with the plant pathogen before the step of contacting, wherein the plant pathogen is a nematode.

14. The method of claim 1, wherein the plant has been infected with the plant pathogen before the step of contacting, wherein the plant pathogen is a microbial plant pathogen.

15. The method of claim 1, wherein the plant is infected with the plant pathogen after the step of contacting, wherein the plant pathogen is a nematode.

16. The method of claim 1, wherein the step of contacting comprises providing the bioprotectant composition admixed with irrigation water, by spraying the bioprotectant composition onto the plant, or the soil or the plant growth media.

17. The method of claim 1, wherein step of contacting comprises contacting the plant or the soil or the plant growth media of the plant with an article comprising the bioprotectant composition.

18. The method of claim 17, wherein the article comprises a biochar, a bead, a filter, a container, a nanoparticle, a microparticle, a mat, a screen, a powder, a particulate, or a cloth.

19. The method of claim 17, wherein the article comprises a woven material, a non-woven material, a plant material, a mat, a container, a polymeric material, a porous material, a non-porous material, or a zeolite.

20. A method for reducing abiotic stress of a plant comprising,
    contacting the plant, or a soil or a plant growth media for the plant, with a bioprotectant composition comprising a cell-free supernatant of a microbial culture and diluent water,
    wherein the cell free supernatant is produced by inoculating IN-M1, deposited under ATCC Accession No. PTA-12383, or IN-M2, deposited under ATCC Accession No. PTA-121556, into a culture media comprising water, molasses, mineral powder, sea salt, and wheat bran; and
    incubating the inoculated culture media for 3-10 weeks at 30-32 or 35-37 or 32-37 degrees Celsius to obtain a microbial culture; and
    centrifuging the microbial culture to separate microbial culture cells from a supernatant; and
    filter sterilizing the supernatant to obtain the cell-free supernatant of the microbial culture, wherein the cell free supernatant comprises high levels of potassium, nitrogen, calcium, and magnesium, and significant levels of volatile fatty acids;
    wherein the ratio between the cell-free supernatant and the diluent water is between 1:25 and 1:1000; and
    wherein the plant has been exposed to abiotic stress, and
    wherein the plant has reduced damage associated with the abiotic stress after the step of contacting with the bioprotectant composition compared to an untreated control plant.

21. The method of claim 20, wherein the bioprotectant composition further comprises an herbicide, a pesticide, a nematocide, a fungicide, a fertilizer, or a nutrient component, or combinations thereof.

* * * * *